United States Patent [19]
Horvitz et al.

[11] Patent Number: 5,929,207
[45] Date of Patent: Jul. 27, 1999

[54] REGULATORS OF G-PROTEIN SIGNALLING

[75] Inventors: H. Robert Horvitz, Auburndale; Michael Koelle, Somerville, both of Mass.

[73] Assignee: Massachusetts Institute of Technology, Cambridge, Mass.

[21] Appl. No.: 08/588,258

[22] Filed: Jan. 12, 1996

[51] Int. Cl.[6] .......................... A61K 38/400; C07K 1/00
[52] U.S. Cl. ............................. 530/324; 530/350
[58] Field of Search ................... 530/350, 351, 530/352; 514/2

[56] References Cited

U.S. PATENT DOCUMENTS

5,225,326  7/1993  Bresser et al. .............................. 435/6

OTHER PUBLICATIONS

Newton et al. (1993) Biochim. Biophys Acta 1216:314–16.
Hong et al. (1993) J. Immunol. 150:3895–3904.
DeVries et al. (1995) Proc Natl Acad Sci USA 92:11916–20.
Siderovsky et al. (1994) DNA Cell Biol. 13:125–47.
Wu et al. (1995) Leukemia 9:1291–98.
Druey et al. (Feb. 1996) Nature 379:742–46.
Dietzel et al., "Pheromonal Regulation and Sequence of the *Saccharomyces cerevisiae* SST2 Gene: a Model for desensitization to Pheromone", Molecular and Cellular Biology 7(12):4169–4177 (1987).
Van Meel et al., "Unexpected contractile response from the G–protein activator mastoparan in cardiac myocytes" European Journal of Pharmacology 247:357–358 (1993).
Penner, "Multiple signaling pathways control stimulus–secretion coupling in rat peritonel mast cells" Proc. Natl. Acad. Sci. USA 85:9856–9860 (1988).
Sham et al., "Signal Pathway Regulation of Interleukin–8–Induced Actin Polymerization in Neutrophils" Blood 82(8):2546–2551 (1993).
Roush, "Regulating G Protein Signaling" Science 271:1056–1058 (1996).
Maniatis al., "Regulation of Inducible and Tissue–Specific Gene Expression" Science 236:1237–1244 (1987).
Jaenisch, "Transgenic Animals" Science 240:1468–1474 (1988).
Wetmur, "DNA Probes: Applications of the principles of Nucleic Acid Hybridization" Critial Reviews in Biochemistry and Molecular Biology 26(3/4):227–259 (1991).
Tung et al. "PCR Technology, Principles and Applications for DNA Amplification" edited by H.A. Erlich, NY, Stockton Press pp. 99–104, (1989).
Braga et al., "Co–Amplification of Two cDNAs in RT–PCR Can Alter the Yield of Both Products" BioTechniques 17(2):228–229 (1994).

Jain et al., "Increasing specificty from the PCR–Race Technique" BioTechniques 12(1):58–59 (1992).
Locus SCDLDG, Accession No. X66052 in Sequence Database embl–new5/genbank 94/genbank–new5/u–embl46_94, from LODI, direct submission by LODI (1993).
Locus YSCEPT1, Accession No. M59311, in Sequence Database embl–new5/genbank 94/genbank–new 5/u–embl46 94, from HJELMSTAD et al. sn–1, 2–diacylglycerol choline– and ethanolaminephosphotransferases in *Saccharomyces cerevisiae*. nucleotide sequence of the EPT1 gene and comparison of the CPT1 and EPT1 gene products. Journal of Biological Chemistry 266(8):5094–5013, (1991).
Locus STAENTD, Accession No. M28521, in Sequence Database embl–new5/genbank 94/genbank–new5/ u–embl46_94, Apr. 3, 1995, from BAYLES et al. Genetics and molecular analyses if the gene encoding *Staphylococcal enterotoxin* D. Journal of Bacteriology 171(9):4799–4806, (1989).
Bauerfeind et al., Biogenesis of Constitutive Secretory Vesicles, Secretory Granules and Synaptic Vesicles.
Bomsel et al., Role of Heterotrimeric G. Proteins in Membrane Traffic. Mol Biol Cell 3:1317–1328, 1992 Curr Opin in Cell Biol 5:628–635, 1993.
Desai et al., A Genetic Pathway for the Development of the *Caenorhabditis elegans* HSN Motor Neurons Nature 336:638–646, 1988.
Desai et al., Caenorhabditis Elegans Mutants Defective in the Functioning of the of the Motor Neurons Responsible for Egg Laying, Genetics 121: 703–721, 1989.
Dietzel et al., Phermonal Regulation and Sequence of the *Saccharomyces cerevisiae* SST2 Gene: A Model for Desensitization to Pheromone, Mol Cell Biol 7:4169–77, 1987.
Fino–Silva et al., Characterization of a G–Protein α Subunit Gene from the Anematode Caenorhabditis Elegans, J Mol Biol 215:483–7, 1990.
Hille, B., G–Protein–Coupled Mechanism and Nervous Signalling, Neuron 9:187–95, 1992.
Lee and Adams, Overexpression of Fiba, an Early Regulator of Aspergillus Assexual Sporulation, Leads to Activation of BRLA and the Premature Initiation of Development, Mol Microbiol 14:323–34, 1994.
Lefkowitz, Clinical Implications of Basic Research: G–Proteins in Medicine. NEJM 332: 186–7, 1995.
Lillie et al., Kinetic Characterization of Guanine–Nucleotide–Induced Exocytosis from Permeabilized Rat Mast Cells, Biochem J 290:389–94, 1993.

(List continued on next page.)

*Primary Examiner*—Bradley L. Sisson
*Attorney, Agent, or Firm*—Clark & Elbing LLP

[57] ABSTRACT

Disclosed is substantially pure DNA encoding a *C. elegans* EGL-10 polypeptide; substantially pure EGL-10 polypeptide; methods of obtaining rgs encoding DNA and RGS polypeptides; and methods of using the rgs DNA and RGS polypeptides to regulate G-protein signalling.

7 Claims, 13 Drawing Sheets

OTHER PUBLICATIONS

Lochrie et al., Homologous and Unique G Protein α Subunits in the Nematode Caenorhabditis Elegans, Cell Regul 2:135–54, 1991.

Mendel et al., Participation of the Protein Go in Multiple Aspects of Behavior in C. Elegans, Science 267:1652–5, 1995.

Nguyen et al., C. Elegans Mutants Resistant to Inhibitors of Acetylcholinesterase, Genetics (in press).

Schwiebert et al., Heterotrimeric G–Proteins, Vesicle Trafficking and CFTR CL Channels, Am J Physiol 267:C272–81, 1994.

Ségalat et al., Modulation of Serotonin–Controlled Behaviors by Go in Caenorhabditis Elegans, Science 267:1648–52, 1995.

Trent et al., Egg–Laying Defective Mutants of the Nematode C. Elegans, Genetics 104: 619–647, 1983.

van der Voorn et al., Characterization of a G–Protein β–Subunit Gene from the Nematode Caenorhabditis Elegans, J. Mol Biol 213:17–26, 1990.

Weiner et al., Disruption of Receptor–G Protein Coupling in Yeast Promotes the Function of an SST2–Dependent Adaptation Pathway, J. Biol Chem 268:8070–77, 1993.

```
  1 TTTGAGACTT TTGTGGCTCA ACACCTCGTT TCTTTTGCAC CCGAACCGCA CCCACGGTAA
 61 CACGGATTCT GCGAGGAATG AAGGAGTAGA AGATAACGGG ACATTCCCTT GTGTCAAAGT
121 GAGAGCCAAC GACGACGATC CTAAGAAGTA TAAACTTGGA AGAGTATTCA CAAAAGTCTT

181 GAAGACTAAA GCTTCACAAT GGCTCTACCA AGATTGAGGG TAAATGCAAG CAACGAGGAG
  1                      M   A   L   P   R   L   R   V   N   A   S   N   E   E

241 CGTCTTGTAC ATCCAAACCA CATGGTGTAC CGTAAGATGG AGATGCTTGT CAATCAAATG
 15   R   L   V   H   P   N   H   M   V   Y   R   K   M   E   M   L   V   N   Q   M

301 CTTGATGCAG AAGCTGGTGT TCCAATCAAG ACTGTCAAGA GTTTTCTGTC AAAAGTTCCA
 35   L   D   A   E   A   G   V   P   I   K   T   V   K   S   F   L   S   K   V   P

361 TCTGTATTCA CCGGACAAGA TCTGATTGGA TGGATCATGA AAAATCTTGA GATGACTGAT
 55   S   V   F   T   [G]  Q   D   L   I   G   W   I   M   K   N   L   E   M   T   D

421 CTTTCGGATG CCCTTCATCT GGCTCATCTG ATCGCGTCAC ACGGTTATCT TTTCCAAATT
 75   L   S   D   A   L   H   L   A   H   L   I   A   S   H   G   Y   L   F   Q   I

481 GACGATCATG TGTTAACGGT TAAAAACGAT GGAACATTCT ATCGGTTTCA AACTCCATAC
 95   D   D   H   V   L   T   V   K   N   D   G   T   F   Y   R   F   Q   T   P   Y

541 TTTTGGCCGT CAAATTGTTG GGATCCGGAA AATACTGATT ACGCGGTGTA CCTGTGCAAG
115   F   W   P   S   N   C   W   D   P   E   N   T   D   Y   A   V   Y   L   C   K

601 CGGACAATGC AGAACAAAGC GCATTTGGAA CTGGAGGACT TTGAAGCGGA GAACCTGGCA
135   R   T   M   Q   N   K   A   H   L   E   L   E   D   F   E   A   E   N   L   A

661 AAGCTGCAGA AGATGTTCTC GCGCAAGTGG GAATTTGTGT TCATGCAAGC CGAAGCTCAA
155   K   L   Q   K   M   F   S   R   K   W   E   F   V   F   M   Q   A   E   A   Q

721 TACAAGGTCG ACAAGAAGCG AGATCGCCAG GAGCGCCAAA TTCTTGACAG TCAGGAACGT
175   Y   K   V   D   K   K   R   D   R   Q   E   R   Q   I   L   D   S   Q   E   R

781 GCTTTCTGGG ATGTTCATCG TCCAGTGCCA GGATGTGTAA ACACTACAGA AGTCGACTTC
195   A   F   [W]  D   V   H   R   P   V   P   G   C   V   N   T   T   E   V   D   F

841 CGGAAGCTTT CACGGTCTGG AAGGCCCAAG TACAGTAGTG GAGGACACGC AGCATTGGCC
215   R   K   L   S   R   S   G   R   P   K   Y   S   S   G   H   A   A   L   A

901 GCTTCAACGT CGGGTATCGG TTGCACTCAG TATTCACAAA GTGTGGCAGC AGCTCATGCG
235   A   S   T   S   G   I   G   C   T   Q   Y   S   Q   S   V   A   A   A   H   A

961 AGTCTTCCAT CAACATCAAA TGGGAGTGCA ACATCTCCAA GAAAGAACGA TCAGGAGCCA
255   S   L   P   S   T   S   N   G   S   A   T   S   P   R   K   N   D   Q   E   P
```

Fig. 2A-1

```
1021  TCAACATCAA GTGGGGGTGA ATCTCCATCA ACATCGTCTG CTGCTGCTGG AACTGCCACA
 275   S  T  S  S   G  G  E   S  P  S   T  S  S   A  A  A  G   T  A  T
                                                            ▼
1081  ACATCTGCAC CATCAACATC AACGCCTCCG GTGACAACTA TTACTGCAAC GATAAATGCA
 295   T  S  A  P   S  T  S   T  P  P   V  T  T  I   T  A  T   I  N  A

1141  GGATCATTCC GAAATAACTA TTACACAAGA CCTGGATTAC GGCGGTGTAC ACAAGTACAG
 315   G  S  F  R   N  N  Y   Y  T  R   P  G  L  R   R  C  T   Q  V  Q

1201  GATACGTTAA AACTGGAAAT TGTGCAATTG AATAGTCGAT TATCAAAAAA TGTATTACGT
 335   D  T  L  K   L  E  I   V  Q  L   N  S  R  L   S  K  N   V  L  R
                              ▼
1261  ACATCTAAAG TTGTAGAAAA TTATTTGGCA TATTACGAAC AACGTCGAGT ATTTGATCCA
 355   T  S  K  V   V  E  N   Y  L  A   Y  Y  E  Q   R  R  V   F  D  P

1321  CTGTTAACGC CTCCTGGATC TCAGGCTGAT CCTTTTCAAT CACAGCCTAA TCCATGGATT
 375   L  L  T  P   P  G  S   Q  A  D   P  F  Q  S   Q  P  N   P (W) I

1381  AACGATACTG TTGATTTTTG GCAACATGAT AAAATTACGG GAGACATCCA AACCCGCCGA
 395   N  D  T  V   D  F  W   Q  H  D   K  I  T  G   D  I  Q   T  R  R
                                                            ▼
1441  CTCAAGCTTT GGGAGGATAG TTTTGAAGAA TTACTTGCTG ATCATTAGG TCCAGAAACT
 415   L  K  L (W)  E  D  S   F  E  E   L  L  A  D   S  L  G   R  E  T

1501  CTTCAAAAAT TCCTTGACAA AGAATATTCT GGAGAAAACT TGCGGTTTTG GTGGGAGGTA
 435   L  Q  K  F   L  D  K   E  Y  S   G  E  N   L  R  F  W   W  E  V

1561  CAAAAGCTGC GAAAGTGCAG TTCAAGAATG GTTCCAGTTA TGGTAACAGA GATTTACAAC
 455   Q  K  L  R   K  C  S   S  R  M   V  P  V  M   V  T  E   I  Y  N

1621  GAGTTTATCG ATACAAATGC GGCAACGTCG CCGGTCAATG TGGATTGTAA AGTGATGGAA
 475   E  F  I  D   T  N  A   A  T  S   P  V  N  V   D  C  K   V  M  E
                                                            ▼
1681  GTGACCGAAG ACAATTTAAA GAATCCAAAT CGGTGGAGTT TTGATGAAGC AGCGGATCAT
 495   V  T  E  D   N  L  K   N  P  N   R (W) S  F   D  E  A   A  D  H

1741  ATCTACTGCC TTATGAAGAA CGATAGTTAT CAACGCTTTC TTCGTTCAGA AATTTATAAG
 515   I  Y  C  L   M  K  N   D  S  Y   Q  R  F  L   R  S  E   I  Y  K

1801  GATTTAGTAT TACAATCAAG AAAGAAGGTA AGTCTCAATT GCTCGTTTTC CATTTTTGCA
 535   D  L  V  L   Q  S  R   K  K  V   S  L  N  C   S  F  S   I  F  A

1861  TCTTGATTCC TCTGAAACCC CTTTCAGTTC CGGTTTTAGC TTAGTTTGAT TCCCACCTTT
 555   S  *
```

Fig. 2A-2

```
1921  TTTCCCTTCC CTTCCCCCAT GAATGTTTTC TTTTCACACT ATGAGATATG TGTTTCATCT
1981  ATTTTTCCGA TTGAAAGCTT ACTGAATGCT CGCTGAAAAA CTTCAAATAA CAAACTCAGA
2041  CCAAATAACA TCAAAGTTCG AGCAATTTAT TTTTTTTATA CCAAAAGCAT GTTCAATTGA
2101  ATATCCCATT CAGTCACTAA CACTCTGATT TCATTCAGTT AATTATATTT TTACAAGTAG
2161  GATCAATACA CCTCAATCCC AATCAATCTA ACACATGTTC ATCCCGATCT CACTAAAATT
2221  TCAACATTTA ATATTTCCAA TCCAAAACCT AAAACGTTAA ACATTTGATC TTGTTTCAAA
2281  TTCAAAATTT CTAACATTG ATTCAGACAA CGTTTACCTC ACTGATTGCT CGTAAAGCAT
2341  CGCGACGCAT CGGATCGACA ATGTCGCGGA GCTCGCAGAG CAACAAAACT CTGCATGCGA
2401  GCGCCTCTCT CGGCTCGGCG CTTTCCGGTC ACGGCTCTTC CACATCATCA ATGCTCACCG
2461  CCGGAGGAGC GGCGTCGAGC CAGAATCTGC TGCTCGCCCC GCCACAACAT CATCTGTATG
2521  TGCCCTCACT CTCTCTCTCA TACACTCACA CTCAACACTC ACTCCCAATG AAATGCAGAA
2581  TGAATGTAGT CTTTTGACAG AAATTGTGGA GAATAGGGAT GAGGAAAAAT GAGGAAAGAT
2641  ATAAGTTTAA AACTTGAAAA ACGTTCCAAA AATTGAAACC AATATTCATT TCTTTCAATA
2701  TCTCTGATCT TTCCAACAAG TCCGGTTCAT TCCACAGACT TTGCAAAATC TCTGTAAAAT
2761  TTTCCTACTT TTTCTTGACG CAACTATGTT CATTCATGTC ATTTGACTTC TCCTCTCATT
2821  GTCCAAAATC TTGTCACTGG TTACATTGGT CACGTCCACA GCGTCACACA TCTTGCAATA
2881  ATCACTAATC ACTTTTTGTC CTGTCACTGT CCAGTCTGCT CTTTCACTGA GTTCACTGA
2941  AATTTTCGAA AGCATGTCAC TTGATTTTTT CGGTTTGCTG CTCACATTGC ACGGCCCTTT
3001  GAATGCACCT GTTGACTTTG GTTTCTGGAA AATACTGAAA ATGTGTTTTG TGTGAATTTG
3061  TAAATCTGAA ATTGCAATGA TTTTGGATGA TTTCATCTTT GAGACTGTTT GCTCTGCTAT
3121  TGTCTTCTCT GAACTACTCG AAAATTTGAA TTGAAAAAAA AAAAAAAA
```

SEQ ID NOS: 27 (NUCLEIC ACID) AND
24 (AMINO ACID)

Fig. 2A-3

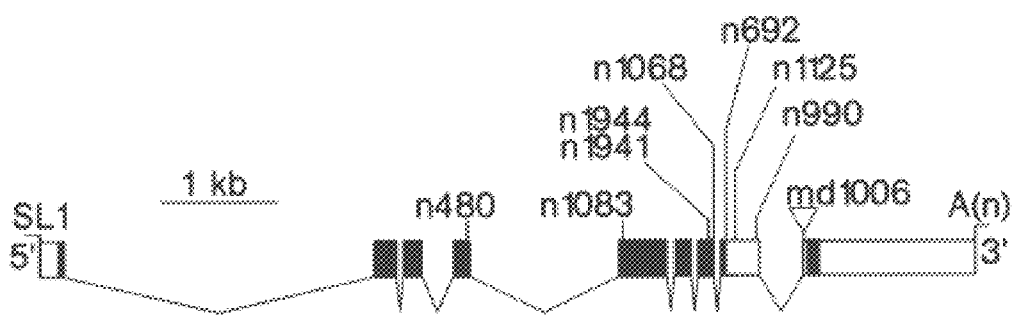
Fig. 2B
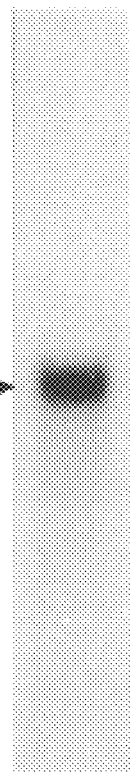
3.2 kb →
Fig. 2C
| Allele | Wild-type sequence | Mutant sequence | Protein change |
|---|---|---|---|
| n480 | GGA | GAA | G58E |
| n1083 | TTCTGG | TTGGGG | W197G |
| n944 | TGG | TAG | W393stop |
| n991 | TGG | TAG | W393stop |
| n1068 | TGG | TGA | W401stop |
| n692 | TGG | TGA | W418stop |
| n1125 | GAA | AAA | E446K |
| n949 | TGG | TAG | W506stop |
| n990 | TGG | TAG | W506stop |
md1006   Tc1 transposon insertion codon 515
md123    rearrangement
md176    rearrangement
md204    rearrangement
md1179   rearrangement
Fig. 2D

Fig. 3B

```
EGL-10    1  MALPRLRVNASNEERLVHPNHMVYRKMEMLVNQMLDAEAGVPIKTVKSFLSKVPSVTGQDLIGWTMKNLEMTDLSDALHLAHLTASHGYLFQDDHVLTVKNDGTFYRFQTPYFWPSNC
hRGS7        ----------------------------------------------------------LSKIPSVFSGGSDIVQMLIKNLTIEDPVEALHLGTLMAAHGYPFPLSDHVLTLKDDGTFYRFQTPYFWPSNC

EGL-10  121  WDPENTDYAVYLCKRTMQNKAHLELEDTEAENLAKLQKMFSRKWEPVFMQAEAQYKVDKKRDQERQILDSQERAFWDVHRPVPGCVNTTEVDPRKLSRSGRPKYSSGGHAALAASTSGI
hRGS7        WEPENTDYAVYLCKRTMQNKARLELADYEAESLARLQRAFARKWEPIFMQAEAQAKVDKKRDKIERKILDSQERAFWDVHRPVPGCVNTTEVDIKKSSRMRNDH----------------

EGL-10  241  GCTQYSQSVAAAHASLPSTSNGSATSPRKNDQEPSTSSGGESPSTSSAAAGTATTSAPSTSTPPVTTTATINAGSFRNNYYTRPGLRRCTQVQDTLKLEIVQLNSRLSKNVLRTSKVVE
hRGS7        --------------------KTPKSVYGLQNDIRSHSPTHFPTPETKPPTEDELQQQIKYWQIQ-------------------------------LDRHRLKMSKVAD

EGL-10  361  NYIAYVEQRRVFDPLLTPGSQADPFQSQPNPWLNDIVDFWQHDKITGDIQTRRLKLMEDSFEELLADSLGRETLQKFLDKEYSGENLRFWEVQXLRKCSSRMVPVMVTIEYMEFLDTN
hRGS7        SLISYTEQYLEVDPPLLPP----DP------SNPWLSDDITEWELEASKEPSQ-QRVMRMGFGMDEALKDPVGREQFLKFLESEFSSENLRFWLAVEDLKKRPIKEVPSRVQEIWQEFL-AP

EGL-10  481  AATSPVNVDCKVMEVTEDNLKNPNRWSTDEAADHIYCLMKNDSYQRTLRSEIYKDIVLQSRKKVSLNC-SFSIFAS
hRGS7        GAPSAINLDSKSYDKITQNVKEPGRVTFEDAQEEIYKLMKSDSYPRFIRSSAYQELLQAKKKGKSLTSKRLTSLAQSY

Fig. 3C
``` rgss-1
ATCAGCTGTGAGGAGTACAAGAAAATCAAATCACCTTCTAAACTAAGTCCCAAGGC
CAAGAAGATCTACAATGAGTTCATCTCTGTGCAGGCAACAAAAGAGGTGAACCTGG
ATTCTTGCACCAGAGAGGAGACAAGCCGGAACATGTTAGAGCCCACGATAACCTGT
TTTGATGAAGCCCGGAAGAAGATTTTCAACCTG                           Seq ID 15 rgss-2
CAGCTTGTAAATGTGCTCCTGAGCATCTTCGAATGTGTATCGTCCTGGTTCCTTCAC
ATTCTGTGTGGTCTTGTCATAACTCTTCGAATCCAAGTTAATGGCACTGGGGGCCCC
CGGAGCCAGAAATTCTTGCCATATTTCCTGTACTCGAGAGGGGACCTCTCGGATAG
GCCTTTTCTTCAGGTCCTCCACTGCCAA                                Seq ID 16 rgss-3
CTGGCCTGTGAGGAGTTCAAGAAGACCAGGTCGACTGCAAAGCTAGTCACCAAGG
CCCACAGGATCTTTGAGGAGTTTGTGGATGTGCAGGCTCCACGGGAGGTGAATATC
GATTTCCAGACCCGAGAGGCCACGAGGAAGAACATGCAGGAGCCGTCCCTGACTT
GTTTTGATCAAGCCCAGGGAAAAGTCCACAGCCTC                         Seq ID 17 rgss-4
GAAGCCTGTGAGGATCTGAAGTATGGGGATCAGTCCAAGGTCAAGGAGAAGGCAG
AGGAGATCTACAAGCTGTTCCTGGCACCGGGTGCAAGGCGATGGATCAACATAGAC
GGCAAAACCATGGACATCACCGTGAAGGGGCTGAGACACCCCCACCGCTATGTGTT
GGACGCGGCGCAGACCCACATTTACATGCTC                             Seq ID 18 rgss-5
CTGGCTTGTGAGGATTTCAAGAAGGTCAAATCGCAGTCCAAGATGGCAGCCAAAGC
CAAGAAGATCTTTGCTGAGTTCATCGCGATCCAGGCTTGCAAGGAGGTAAACCTGG
ACTCGTACACACGAGAACACACTAAGGAGAACCTGCAGAGCATCACCCGAGGCTG
CTTTGACCTGGCACAAAAACGTATCTTCGGGCTC                          Seq ID 19 rgss-6
GTTGCCTGTGAGAATTACAAGAAGATCAAGTCCCCCATCAAAATGGCAGAGAAGGC
AAAGCAAATCTATGAAGAATTCATCCAGACAGAGGCCCCTAAAGAGGTGAACATT
GACCACTTCACTAAAGACATCACCATGAAGAACCTGGTGGAACCTTCCCCTCACAG
CTTTGACCTGGCCCAGAAAAGGATCTACGCCCTG                          Seq ID 20

Fig. 5-1 rgss-7
CTGGCCGTCCAAGATCTCAAGAAGCAACCTCTACAGGATGTGGCCAAGAGGGTGG
AGGAAATCTGGCAAGAGTTCCTAGCTCCCGGAGCCCCAAGTGCAATCAACCTGGAT
TCTCACAGCTATGAGATAACCAGTCAGAATGTCAAAGATGGAGGGAGATACACATT
TGAAGATGCCCAGGAGCACATCTACAAGCTG                                  Seq ID 21 rgss-8
CTAGCGTGTGAAGATTTCAAGAAAACGGAGGACAAGAAGCAGATGCAGGAAAAGG
CCAAGAAGATCTACATGACCTTCCTGTCCAATAAGGCCTCTTCACAAGTCAATGTG
GAGGGGCAGTCTCGGCTCACTGAAAAGATTCTGGAAGAACCACACCCTCTGATGTT
CCAAAAGCTCCAGGACCAGATCTTCAATCTC                                  Seq ID 22 rgss-9
GAGGCGTGTGAGGAGCTGCGCTTTGGCGGACAGGCCCAGGTCCCCACCCTGGTGGA
CTCTGTTTACCAGCAGTTCCTGGCCCCTGGAGCTGCCCGCTGGATCAACATTGACA
GCAGAACAATGGAGTGGACCCTGGAGGGGCTGCGCCAGCCACACCGCTATGTCCT
AGATGCAGCACAACTGCACATCTACATGCTC                                  Seq ID 23

Fig. 5-2

SEQ ID NO: 41

```
   1 tctttccaag atacctagcg tcttctctgg ttcagacatt gttcaatggt tgataaagaa
  61 cttaactata gaagatccag tggaggcgct ccatttggga acattaatgg ctgcccacgg
 121 ctacttcttt ccaatctcag atcatgtcct cacactcaag gatgatggca ccttttaccg
 181 gtttcaaacc ccctatttt ggccatcaaa ttgttgggag ccggaaaaca cagattatgc
 241 cgtttacctc tgcaagagaa caacgcaaaa caaggcacga ctggagctcg cagactatga
 301 ggctgagagc ctggccaggc tgcagagagc atttgcccgg aagtggggagt tcattttcat
 361 gcaagcagaa gcacaagcaa aagtggacaa gaagagagac aagattgaaa ggaagatcct
 421 tgacagccaa gagagagcgt tctgggacgt gcacaggccc gtgcctggat gtgtaaatac
 481 aactgaagtg gacattaaga agtcatccag aatgagaaac ccccacaaaa cacggaagtc
 541 tgtctatggt ttacaaaatg atattagaag tcacagtcct acccacacac ccacaccaga
 601 aactaaacct ccaacagaag atgagttaca acaacagata aaatattggc aaatacagtt
 661 agatagacat cggttaaaaa tgtcaaaagt cgctgacagt ctactaagtt acacggaaca
 721 gtatttagaa tacgacccgt ttcttttgcc acctgacccct tctaacccat ggctgtccga
 781 tgacaccact ttctgggaac ttgaggcaag caaagaaccg agccagcaga gggtaaaacg
 841 atggggtttt ggcatggacg aggcattgaa agacccagtt gggagagaac agttccttaa
 901 atttctagag tcagaattca gctcggaaaa tttaagattc tggctggcag tggaggacct
 961 gaaaaagagg cctattaaag aagtaccctc aagagttcag gaaatatggc aagagtttct
1021 ggctcccgga gcccccagtg ctattaactt ggattccaag agttatgaca aaaccacaca
1081 gaacgtgaag gaacctggac gatacacatt tgaagatgct caggagcaca tttacaaact
1141 gatgaaaagt gattcatacc cacgttttat aagatccagt gcctatcagg agcttctaca
1201 ggcaaagaaa aaggggaaat ctctcacgtc caagaggtta acaagccttg ctcagtctta
1261 ctaaacggat catcttgtag catgaatgca gactggagtc actgcacaca ctttgtagct
1321 caatgttgtg acctggagca gaggacatta gaacaagatg ttgcatgagc aaaggaccta
1381 aattgttatt tttgtgtgta cattccatct ccaatggact cttccgtctc aatgcctcca
1441 ttccaaactg ttgtctgctt tcttctcct tctactatgc tggatctgtg tctcttcctt
1501 tttaacaagt tcaagtgaag taaaacccttt tctttttttc cttctttctc tctctctctc
1561 tctcaaagct ccagttagac acacagttca ctgaaaattc agtcagtcaa aaactggaag
1621 aactgtaaaa gaaaaagta catatcaata agtatacatg tggcttcaca tttattaaac
1681 aataaattcc gcacagaaag tttcatttca ccaatgtgtc acagtcagaa acaaactcat
1741 gtcttcgtca gctgtccgca cattccccgt taatgcttct cgcatttatt tttataccac
1801 atttaaagaa gaaacacctt ttactccaaa tgtattaaag ttgatccctt ctctgtaaat
1861 ttgtgtatgt ttatattgtt gttttatctt tcattgaaag atgcagaatc tcc
```

Fig. 7

REGULATORS OF G-PROTEIN SIGNALLING

STATEMENT AS TO FEDERALLY SPONSORED RESEARCH

Work described herein was supported by NIH grant R37GM24663. The U.S. Government has certain rights in the invention.

BACKGROUND OF THE INVENTION

The invention relates to regulators of heterotrimeric G-protein mediated events and uses thereof to mediate cell signalling and membrane trafficking.

The heterotrimeric guanine nucleotide binding proteins (G proteins) are intracellular proteins best known for their role as transducers of binding by extracellular ligands to seven transmembrane receptors (7-TMRs) located on the cell surface. Individual 7-TMRs have been identified for many small neurotransmitters (e.g. adrenaline, noradrenaline, dopamine, serotonin, histamine, acetylcholine, GABA, glutamate, and adenosine), for a variety of neuropeptides and hormones (e.g. opioids, tachykinins, bradykinins, releasing hormones, vasoactive intestinal peptide, neuropeptide Y, thyrotrophic hormone, leutenizing hormone, follicle-stimulating hormone, adrenocorticotropic hormone, cholecystokinin, gastrin, glucagon, somatostatin, endothelin, vasopressin and oxytocin) as well as for chemoattractant chemokines (C5a, interleukin-8, platelet-activating factor and the N-formyl peptides) that are involved in immune function. In addition, the odorant receptors present on vertebrate olfactory cells are 7-TMRs, as are rhodopsins, the proteins that transduce visual signals.

Ligand binding to 7-TMRs produces activation of one or more heterotrimeric G-proteins. A few proteins with structures that are dissimilar to the 7-TMRs have also been shown to activate heterotrimeric G-proteins. These include the amyloid precursor protein, the terminal complement complex, the insulin-like growth factor/mannose 6-phosphate receptor and the ubiquitous brain protein GAP-43. Dysregulation of G-protein coupled pathways is associated with a wide variety of diseases, including diabetes, hyperplasia, psychiatric disorders, cardiovascular disease, and possibly Alzheimer's disease. Accordingly, the 7-TMRs are targets for a large number of therapeutic drugs: for example, the β-adrenergic blockers used to treat hypertension target 7-TMRS.

Unactivated heterotrimeric G-proteins are complexes comprised of three subunits, Gα, Gβ and Gγ. The subunits are encoded by three families of genes: in mammals there are at least 15 Gα, 5 Gβ and 7 Gγ genes. Additional diversity is generated by alternate splicing. Where it has been studied, a similar multiplicity of G-proteins has been found in invertebrate animals. Mutations within Gα subunit genes is involved in the pathophysiology of several human diseases: mutations of Gα that activate Gs or Gi2 are observed in some endocrine tumors and are responsible for McCune-Albright syndrome, whereas loss-of-function mutations of Gαs are found in Albright hereditary osteodystrophy.

The Gα subunits have binding sites for a guanine nucleotide and intrinsic GTPase activity. This structure and associated mechanism are shared with the monomeric GTP-binding proteins of the ras superfamily. Prior to activation the complex contains bound GDP: GαGDPβγ. Activation involves the catalyzed release of GDP followed by binding of GTP and concurrent dissociation of the complex into two signalling complexes: GαGTP and βγ. Signalling through GαGTP, the more thoroughly characterized pathway, is terminated by GTP hydrolysis to GDP. GαGDP then reassociates with βγ to reform the inactive, heterotrimeric complex.

The mammalian G-proteins are divided into four subtypes: Gs, Gi/Go, Gq and G12. This typing is based on the effect of activated G-proteins on enzymes that generate second messengers and on their sensitivity to cholera and pertussis toxin. These divisions also appear to be evolutionarily ancient: there are comparable subtypes in invertebrate animals. Members of two subtypes of G-proteins control the activity of adenylyl cyclases (ACs). Activated Gs proteins increase the activity of ACs whereas activated Gi proteins (but not Go) inhibit these enzymes. Gs proteins are also uniquely activated by cholera toxin. ACs are the enzymes responsible for the synthesis of cyclic adenosine monophosphate (cAMP). cAMP is a diffusible second messenger that acts through cAMP-dependent protein kinases (PKAs) to phosphorylate a large number of target proteins. Members of two subtypes, all Gi/Go proteins and the Gq proteins, increase the activity of inositol phospholipid-specific phospholipases (IP-PLCs). The activity of the subtypes are distinguishable: activation of Gi and Go are blocked by pertussis toxin whereas Gq is resistant to this compound. IP-PLCs release two diffusible second messengers, inositol triphosphate ($IP_3$) and diacylglycerol (DAG). $IP_3$ modulates intracellular $Ca^{2+}$ concentration whereas DAG activates protein kinase Cs (PKCs) to phosphorylate many target proteins. The second messenger cascades allow signals generated by G-protein activation to have global effects on cellular physiology.

Activation of G proteins frequently modulate ion conductance through plasma membrane ion channels. Although in some cases these effects are indirect, as a result of changes in second messengers, G-proteins can also couple directly to ion channels. This phenomenon is known as membrane delimited modulation. The opening of inwardly rectifying K channels by activated Gi/Go and of N and L type Ca channels by Gi/Go and Gq are commonly observed forms of membrane delimited modulation.

Heterotrimeric G proteins appear to have other cellular roles, in addition to transducing the binding of extracellular ligands. Analysis of the intracellular localization of the various G-protein subunits combined with pharmacological studies suggest, for example, that G proteins are involved in intracellular membrane trafficking. Indeed, some workers hypothesize that G proteins evolved to control membrane trafficking and that their role in transducing extracellular signals evolved later. Studies implicate heterotrimeric G-proteins in the formation of vesicles from the trans-Golgi network, in transcytosis in polarized epithelial cells and in the control of secretion in many cells, including several model systems relevant to human disease: mast cells, chromaffin cells of the adrenal medulla and human airway epithelial cells. Nonetheless, the G-protein subunits involved in membrane trafficking and secretion have yet to be definitively established and the mechanisms by which they are activated and control membrane trafficking remains largely unknown.

*Caenorhabditis elegans* (reviewed in Wood, et al. (1988) *The Nematode Caenorhabditis elegans*. Cold Spring Harbor Press, Cold Spring Harbor, N.Y.) is a small free-living nematode which grows easily and reproduces rapidly in the laboratory. The adult *C. elegans* has about 1000 somatic cells (depending on the sex). The anatomy of *C. elegans* is relatively simple and extremely well-known, and its developmental cell lineage is highly reproducible and completely determined. There are two sexes: hermaphrodites that produce both eggs and sperm and are capable of self fertilization and males that produce sperm and can productively mate with the hermaphrodites. The self fertilizing mode of reproduction greatly facilitates the isolation and analysis of genetic mutations and *C. elegans* has developed into a most powerful animal model system. In addition, *C. elegans* has a small genome (~$10^8$ base pairs) whose sequencing is more advanced than that of any other animal.

Genes that encode G-protein subunits in *C. elegans* were identified using probes to sequences conserved in corresponding mammalian genes. So far six Gα genes have been identified including the nematode homologs of mammalian Gαs, Gαo and Gαq/11 as well as three putative Gα proteins that have not yet been assigned to a mammalian subtype class. Gαo, is encoded by the gene goa-1. The Gαo protein from *C. elegans* is 80–87% identical to homologous proteins from other species. Mutations that reduce the function of goa-1 cause behavioral defects in *C. elegans* including hyperactive locomotion, premature egg-laying, inhibition of pharyngeal pumping, male impotence, a reduction in serotonin-induced inhibition of defecation and reduced fertility. Mutations of goa-1 homologous to the known activating mutations of mammalian Gαs and Gαi2 or overexpression of wild type goa-1 caused behavioral defects which appear to be opposite to those conferred by reducing goa-1 function: sluggish locomotion, delayed egg-laying and hyperactive pharyngeal pumping.

egl-10 is a gene from *C. elegans*, originally identified by mutations that cause defects in egg-laying behavior (C. Trent, N. Tsung and H. R. Horvitz (1983) Genetics 104:619–647). The egg-laying defect appears to involve a pair of serotonergic motor neurons (the HSN cells) which innervate vulva muscles in *C. elegans* hermaphrodites (C. Desai, G. Garriga, S. L. McIntire and H. R. Horvitz (1988) Nature 336:638–646; C. Desai and H. R. Horvitz (1989) Genetics 121:703–7212).

SUMMARY OF THE INVENTION

We have discovered a new family of proteins involved in the control of heterotrimeric G-protein mediated effects in both mammalian and non-mammalian cells. We disclose sequences which comprise the conserved domains of nine members of this family and methods for identifying additional members. We have named this family of proteins RGS proteins for Regulators of G-protein Signalling.

In general, the invention features substantially pure nucleic acid (for example, genomic DNA, cDNA, RNA or synthetic DNA) encoding an RGS polypeptide as defined below. In related aspects, the invention also features a vector, a cell (e.g., a bacterial, yeast, nematode, or mammalian cell), and a transgenic animal which includes such a substantially pure DNA encoding an RGS polypeptide.

In preferred embodiments, an rgs gene is the egl-10 gene of a nematode of the genus *C. elegans* or the human homolog, rgs7. In another preferred embodiment, the RGS encoding nucleic acid cell is in a transformed animal cell. In related aspects, the invention features a transgenic animal containing a transgene which encodes an RGS polypeptide that is expressed in animal cells which undergo G-protein mediated events (for example, responses to neuropeptides, hormones, chemoattractant chemokines, and odor, and synthetic or naturally responses to opiates).

In a second aspect, the invention features a substantially pure DNA which includes a promoter capable of expressing the rgs gene in a cell. In preferred embodiments, the promoter is the promoter native to an rgs gene. Additionally, transcriptional and translational regulatory regions are preferably native to an rgs gene.

In another aspect, the invention features a method of detecting a rgs gene in a cell involving: (a) contacting the rgs gene or a portion thereof greater than 9 nucleic acids, preferably greater than 18 nucleic acids in length with a preparation of genomic DNA from the cell under hybridization conditions providing detection of DNA sequences having about 30% or greater sequence identity among the amino acid sequences encoded by the conserved DNA sequences of FIG. 3B or the sequences of sequence ID Nos. 2–5 and the nucleic acid of interacting. Preferably, the region of sequence identity used for hybridization is the DNA sequence encoding one of the sequences in the shaded region depicted in FIG. 3B (e.g., the DNA encoding amino acids 1–43 and 92–120 of the EGL-10 fragment shown in FIG. 3B (SEQ ID NO: 1)). More preferably, the region of identity is to the DNA encoding the polypeptide sequence delineated by the solid black in FIG. 3B (e.g., amino acids 36–43 and 92–102 of the EGL-10 sequence shown in FIG. 3B). Even more preferably the sequence identity is to the sequences of ID Nos. 1–5. Most preferably, the sequence identity is to the sequences of SEQ ID NOS: 33 or 34. Most preferably, the sequence identity of the nucleic acid sequences being compared is 50%.

In another aspect, the invention features a method of producing an RGS polypeptide which involves: (a) providing a cell transformed with DNA encoding an RGS polypeptide positioned for expression in the cell (for example, present on a plasmid or inserted in the genome of the cell); (b) culturing the transformed cell under conditions for expressing the DNA; and (c) isolating the RGS polypeptide.

In another aspect, the invention features substantially pure RGS polypeptide. Preferably, the polypeptide includes a greater than 50 amino acid sequence substantially identical to a greater than 50 amino acid sequence shown in the FIG. 2, open reading frame, more preferably the identity is to one of the conserved regions of homology shown in FIG. 3B (e.g., the sequences 1–43 and 92–120) and, more preferably, 36–43 and 92–102 of SEQ ID NO: 1 and most preferably, the identity is to one of the sequences shown in SEQ ID NOS: 2–5.

In another aspect, the invention features a method of regulating G-protein mediated events wherein the method involves: (a) providing the rgs gene under the control of a promoter providing controllable expression of the rgs gene in a cell wherein the rgs gene is expressed in a construct capable of delivering an RGS protein in an amount effective to alter said G-protein mediated events. The polypeptide may also be provided directly, for example, in cell culture and therapeutic uses. In preferred embodiments, the rgs gene is expressed using a tissue-specific or cell type-specific promoter, or by a promoter that is activated by the introduction of an external signal or agent, such as a chemical signal or agent.

In other aspects, the invention features a substantially pure oligonucleotide including one or a combination of the sequences:

5' GNIGANAARYTIGANTTRTGG 3', wherein N is G or A; R is T or C; and Y is A, T, or C (SEQ ID NO: 2);

5' GNIGANAARYTISGITTRTGG 3', wherein N is G or A; R is T or C; Y is A, T, or C; and S is A or C (SEQ ID NO: 3);

5' GNTAIGANTRITTRTRCAT 3', wherein N is G or A; and R is T or C (SEQ ID NO: 4);

5' GNTANCTNTRITTRTRCAT 3', wherein N is G or A; and R is T or C (SEQ ID NO: 5);

the egl-10 DNA shown in FIG. 2A (SEQ ID NO: 27);

ATCAGCTGTGAGGAGTACAAGAAAATCAAATCACCTTCTAAACTAAGTCCCAAGGC (SEQ ID NO: 15)
CAAGAAGATCTACAATGAGTTCATCTCTGTGCAGGCAACAAAAGAGGTGAACCTGG
ATTCTTGCACCAGAGAGGAGACAAGCCGGAACATGTTAGAGCCCACGATAACCTGT
TTTGATGAAGCCCGGAAGAAGATTTTCAACCTG;

CAGCTTGTAAATGTGCTCCTGAGCATCTTCGAATGTGTATCGTCCTGGTTCCTTCAC (SEQ ID NO: 16)
ATTCTGTGTGGTCTTGTCATAACTCTTCGAATCCAAGTTAATGGCACTGGGGCCCC
CGGAGCCAGAAATTCTTGCCATATTTCCTGTACTCGAGAGGGGACCTCTCGGATAG
GCCTTTTCTTCAGGTCCTCCACTGCCAA;

CTGGCCTGTGAGGAGTTCAAGAAGACCAGGTCGACTGCAAAGCTAGTCACCAAGG (SEQ ID NO: 17)
CCCACAGGATCTTTGAGGAGTTTGTGGATGTGCAGGCTCCACGGGAGGTGAATATC
GATTTCCAGACCCGAGAGGCCACGAGGAAGAACATGCAGGAGCCGTCCCTGACTT
GTTTTGATCAAGCCCAGGGAAAAGTCCACAGCCTC;

GAAGCCTGTGAGGATCTGAAGTATGGGGATCAGTCCAAGGTCAAGGAGAAGGCAG (SEQ ID NO: 18)
AGGAGATCTACAGGCTGTTCCTGGCACCGGGTGCAAGGCGATGGATCAACATAGAC
GGCAAAACCATGGACATCACCGTGAAGGGGCTGAGACACCCCCACCGCTATGTGTT
GGACGCGGCGCAGACCCACATTTACATGCTC;

CTGGCTTGTGAGGATTTCAAGAAGGTCAAATCGCAGTCCAAGATGGCAGCCAAAGC (SEQ ID NO: 19)
CAAGAAGATCTTTGCTGAGTTCATCGCGATCCAGGCTTGCAAGGAGGTAAACCTGG
ACTCGTACACACGAGAACACACTAAGGAGAACCTGCAGAGCATCACCCGAGGCTG
CTTTGACCTGGCACAAAAACGTATCTTCGGGCTC;

GTTGCCTGTGAGAATTACAAGAAGATCAAGTCCCCCATCAAAATGGCAGAGAAGGC (SEQ ID NO: 20)
AAAGCAAATCTATGAAGAATTCATCCAGACAGAGGCCCCTAAAGAGGTGAACATT
GACCACTTCACTAAAGACATCACCATGAAGAACCTGGTGGAACCTTCCCCTCACAG
CTTTGACCTGGCCCAGAAAAGGATCTACGCCCTG;

CTGGCCGTCCAAGATCTCAAGAAGCAACCTCTACAGGATGTGGCCAAGAGGGTGG (SEQ ID NO: 21)
AGGAAATCTGGCAAGAGTTCCTAGCTCCCGGAGCCCCAAGTGCAATCAACCTGGAT
TCTCACAGCTATGAGATAACCAGTCAGAATGTCAAAGATGGAGGGAGATACACATT
TGAAGATGCCCAGGAGCACATCTACAAGCTG;

CTAGCGTGTGAAGATTTCAAGAAAACGGAGGACAAGAAGCAGATGCAGGAAAAGG (SEQ ID NO: 22)
CCAAGAAGATCTACATGACCTTCCTGTCCAATAAGGCCTCTTCACAAGTCAATGTG
GAGGGGCAGTCTCGGCTCACTGAAAAGATTCTGGAAGAACCACACCCTCTGATGTT
CCAAAAGCTCCAGGACCAGATCTTCAATCTC;

and

GAGGCGTGTGAGGAGCTGCGCTTTGGCGGACAGGCCCAGGTCCCCACCCTGGTGGA (SEQ ID NO: 23)
CTCTGTTTACCAGCAGTTCCTGGCCCCTGGAGCTGCCCGCTGGATCAACATTGACA
GCAGAACAATGGAGTGGACCCTGGAGGGGCTGCGCCAGCCACACCGCTATGTCCT
AGATGCAGCACAACTGCACATCTACATGCTC.

In another aspect, the invention features a substantially pure polypeptide including one or a combination of the amino acid sequences:

$Xaa_1$ $Xaa_2$ $Xaa_3$ Glu $Xaa_4$ $Xaa_5$ $Xaa_6$ $Xaa_7$, wherein $Xaa_1$ is I, L, E, or V, preferably L; $Xaa_2$ is A, S, or E, preferably A; $Xaa_3$ is C or V, preferably C; $Xaa_4$ is D, E, N, or K, preferably D; Xaa$_5$ is L, Y, or F; Xaa$_6$ is K or R, preferably R; and Xaa$_7$ is K, R, Y, or F, preferable K (SEQ ID NO: 25); and Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Lys, wherein Xaa$_1$ is F or L, preferably F; Xaa$_2$ is D, E, T, or Q, preferably D; Xaa$_3$ is E, D, T, Q, A, L, or K; Xaa$_4$ is A or L, preferably A; Xaa$_5$ is Q or A, preferably Q; Xaa$_6$=L, D, E, K, T, G, or H; Xaa$_7$ is H, R, K, Q or D; Xaa$_8$ is I or V, preferably I; Xaa$_9$=Q, T, S, N, K, M, G or A (SEQ ID NO: 26). More preferably, the sequences are LACEDXaaK, wherein Xaa is L, Y, or F and (SEQ ID NO: 33) FDXaa,AQXaa$_2$Xaa$_3$IXaa$_4$, wherein Xaa, is E, D, T, Q, A, L, or K; Xaa$_2$ is L, D, E, K, T, G, or H; and Xaa$_3$ is H, R, K, Q, or D (SEQ ID NO: 34).

In preferred embodiments the invention features polypeptides having the sequences substantially identical to the EGL-10 and the human RGS2 polypeptides shown in FIG. 3C. More preferably, the polypeptides are identical to the sequences of EGL-10 and human RGS2 provided in FIG. 3C.

In another aspect, the invention features a method of isolating a rgs gene or fragment thereof from a cell, involving: (a) providing a sample of cellular DNA; (b) providing a pair of oligonucleotides having sequence homology to a conserved region of an rgs gene (for example, the oligonucleotides of SEQ ID NOS: 2–5); (c) combining the pair of oligonucleotides with the cellular DNA sample under conditions suitable for polymerase chain reaction-mediated DNA amplification; and (d) isolating the amplified rgs gene or fragment thereof. Where a fragment is obtained by PCR standard library screening techniques may be used to obtain the complete coding sequence. In preferred embodiments, the amplification is carried out using a reverse-transcription polymerase chain reaction, for example, the RACE method.

In another aspect, the invention features a method of identifying a rgs gene in a cell, involving: (a) providing a preparation of cellular DNA (for example, from the human genome); (b) providing a detectably-labelled DNA sequence (for example, prepared by the methods of the invention) having homology to a conserved region of an rgs gene; (c) contacting the preparation of cellular DNA with the detectably-labelled DNA sequence under hybridization conditions providing detection of genes having 50% or greater sequence identity; and (d) identifying an rgs gene by its association with the detectable label.

In another aspect, the invention features a method of isolating an rgs gene from a recombinant DNA library, involving: (a) providing a recombinant DNA library; (b) contacting the recombinant DNA library with a detectably-labelled gene fragment produced according to the PCR method of the invention under hybridization conditions providing detection of genes having 50% or greater sequence identity; and (c) isolating a member of an rgs gene by its association with the detectable label.

In another aspect, the invention features a method of isolating an rgs gene from a recombinant DNA library, involving: (a) providing a recombinant DNA library; (b) contacting the recombinant DNA library with a detectably-labelled RGS oligonucleotide of the invention under hybridization conditions providing detection of genes having 50% or greater sequence identity; and (c) isolating an rgs gene by its association with the detectable label.

In another aspect, the invention features a recombinant polypeptide capable of altering G-protein mediated events wherein the polypeptide includes a domain having a sequence which has at least 70% identity to at least one of the sequences of sequence ID Nos. 1, 6–14, 25 or 26. More preferably, the region of identity is 80% or greater, most preferably the region of identity is 95% or greater.

In another aspect, the invention features an rgs gene isolated according to the method involving: (a) providing a sample of cellular DNA; (b) providing a pair of oligonucleotides having sequence homology to a conserved region of an rgs gene; (c) combining the pair of oligonucleotides with the cellular DNA sample under conditions suitable for polymerase chain reaction-mediated DNA amplification; and (d) isolating the amplified rgs gene or fragment thereof.

In another aspect, the invention features an rgs gene isolated according to the method involving: (a) providing a preparation of cellular DNA; (b) providing a detectably-labelled DNA sequence having homology to a conserved region of an rgs gene; (c) contacting the preparation of DNA with the detectably-labelled DNA sequence under hybridization conditions providing detection of genes having 50% or greater sequence identity; and (d) identifying an rgs gene by its association with the detectable label.

In another aspect, the invention features an rgs gene isolated according to the method involving: (a) providing a recombinant DNA library; (b) contacting the recombinant DNA library with a detectably-labelled rgs gene fragment produced according to the method of the invention under hybridization conditions providing detection of genes having 50% or greater sequence identity; and (c) isolating an rgs gene by its association with the detectable label.

In another aspect, the invention features a method of identifying an rgs gene involving: (a) providing a mammalian cell sample; (b) introducing by transformation (e.g. biolistic transformation) into the cell sample a candidate rgs gene; (c) expressing the candidate rgs gene within the cell sample; and (d) determining whether the cell sample exhibits an alteration in G-protein mediated response, whereby a response identifies an rgs gene.

Preferably, the cell sample used herein is selected from cardiac myocytes or other smooth muscle cells, neutrophils, mast cells or other myeloid cells, insulin secreting β-cells, COS-7 cells, or xenopus oocytes. In other preferred embodiments the candidate rgs gene is obtained from a cDNA expression library, and the RGS response is a membrane trafficking or secretion response or an alteration on [H$^3$] IP3 or cAMP Levels.

In another aspect, the invention features an rgs gene isolated according to the method involving: (a) providing a cell sample; (b) introducing by transformation into the cell sample a candidate rgs gene; (c) expressing the candidate rgs gene within the tissue sample; and (d) determining whether the tissue sample exhibits a G-protein mediated response or decrease thereof, whereby a response identifies an rgs gene.

In another aspect, the invention features a purified antibody which binds specifically to an RGS family protein. Such an antibody may be used in any standard immunodetection method for the identification of an RGS polypeptide.

In another aspect, the invention features a DNA sequence substantially identical to the DNA sequence shown in FIG. 2A. In a related aspect, the invention features a DNA sequence substantially identical to the DNA sequence shown in FIG. 7.

In two additional aspects, the invention features a substantially pure polypeptides having sequences substantially identical to amino acid sequences shown in FIG. 3C (SEQ ID NOS:27 and 40).

In another aspect, the invention features a kit for detecting compounds which regulate G-protein signalling. The kit includes RGS encoding DNA positioned for expression in a cell capable of producing a detectable G-protein signalling response. Preferably, the cell is a cardiac myocyte, a mast cell, or a neutrophil.

In a related aspect, the invention features a method for detecting a compound which regulates G-protein signalling. The method includes:

i) providing a cell having RGS encoding DNA positioned for expression; ii) contacting the cell with the compound to be tested; iii) monitoring the cell for an alteration in G-protein signalling response.

Preferably, the cell used in the method is a cardiac myocyte, a mast cell, or a neutrophil, and the responses assayed are an electrophysical response, a degranulation response, or IL-8 mediated response, respectively.

For aforementioned methods involving the use of RGS proteins or rgs genes it is noted that the use IR-20/BL34 or gos-8 nucleic acids or proteins encoded there from are also included as methods of the invention. Preferably 1R20/BL34 and gos-8 nucleic and encoded proteins are used in methods for regulating G-proein signalling.

By "rgs" is meant a gene encoding a polypeptide capable of altering a G-protein mediated response in a cell or a tissue and which has at least 50% or greater identity to the conserved regions described in FIG. 3B. The preferred regions of identity are as described below under "conserved regions." An rgs gene is a gene including a DNA sequence having about 50% or greater sequence identity to the RGS sequences which encode the conserved polypeptide regions shown in FIG. 3B and described below, and which encodes a polypeptide capable of altering a G-protein mediated response. EGL-10 and the human rgs2 are examples of rgs genes encoding the EGL-10 polypeptide from *C. elegans* and a human RGS polypeptide, respectively.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine and tyrosine.

By a "substantially pure polypeptide" is meant an RGS polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, RGS polypeptide. A substantially pure RGS polypeptide may be obtained, for example, by extraction from a natural source (e.g., a human or rat cell); by expression of a recombinant nucleic acid encoding an RGS polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an RGS polypeptide.

By "positioned for expression" is meant that the DNA molecule is positioned adjacent to a DNA sequence which directs transcription and translation of the sequence (i.e., facilitates the production of, e.g., an RGS polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic rodents and the DNA (transgene) is inserted by artifice into the genome.

By an "rgs gene" is meant any member of the family of genes characterized by their ability to regulates a G-protein mediated response and having at least 20%, preferably 30%, and most preferably 50% amino acid sequence identity to one of the conserved regions of one of the RGS members described herein (i.e., either the egl-10 gene or the rgs 1-9 gene sequences described herein). rgs gene family does not include the FlbA, the Sst-2, CO5B5.7, GOS-8, BL34 (also referred as 1R20) gene sequences.

By "conserved region" is meant any stretch of six or more contiguous amino acids exhibiting at least 30%, preferably 50%, and most preferably 70% amino acid sequence identity between two or more of the RGS family members. Examples of preferred conserved regions are shown (as overlapping or designated sequences) in FIGS. 3A and 3B and include the sequences provided by seq ID Nos. 2–5, 25 and 26. Preferably, the conserved region is a region shown by shading blocks in FIG. 3B (e.g., amino acids 1–43 and 92–120 of the EGL-10 sequence shown in FIG. 3B (SEQ ID NO: 1). More preferably, the conserved region is the region delineated by a solid block in FIG. 3B (e.g., amino acids 36–43 and 92–102 of the EGL-10 sequence of FIG. 3B). Even more preferably, the conserved region is defined by the sequences of SEQ ID NOS: 1–5. Most preferably, the sequences are defined by the sequences of SEQ ID NOS: 33 and 34.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "transformation" is meant any delivery of DNA into a cell. Methods for delivery of DNA into a cell are well known in the art and include, without limitation, viral transfer, electroportion, lipid mediated transfer and biolistic transfer.

By "biolistic transformation" is meant any method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles, bacteria, yeast, fungi, algae, pollen, animal tissue, plant tissue and cultured cells.

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., an EGL-10 specific antibody. A purified RGS antibody may be obtained, for example, by affinity chromatography using recombinantly-produced RGS protein or conserved motif peptides and standard techniques.

By "specifically binds" is meant an antibody which recognizes and binds an RGS protein but which does not substantially recognize and bind other molecules in a sample, e.g., a biological sample, which naturally includes RGS protein.

By "regulating" is meant conferring a change (increase or decrease) in the level of a G-protein mediated response relative to that observed in the absence of the RGS polypeptide, DNA encoding the RGS polypeptide, or test compound. Preferably, the change in response is at least 5%, more preferably, the change in response is greater than 20%, and most preferably, the change in response level is a change of more than 50% relative to the levels observed in the absence of the RGS compound or test compound.

By "G-protein signalling response" is meant a response mediated by heterotrimeric guanine nucleotide binding proteins. It will be appreciated that these responses and assays for detecting these responses are well-known in the art. For example, many such responses are described in the references provided in the detailed description, below.

By an "effective amount" is meant an amount sufficient to regulate a G-protein mediated response. It will be appreciated that there are many ways known in the art to determine the effective amount for a given application. For example, the pharmacological methods for dosage determination may be used in the therapeutic context.

Other features and advantages of the invention will be apparent from the following description of the preferred embodiments thereof, and from the claims.

DETAILED DESCRIPTION

The drawings will first be described.
Drawings

FIG. 2A is the nucleotide sequence of egl-10 cDNA and the amino acid sequence from the open reading frame, EGL-10 (SEQ ID NO: 27. ADD SEQ NO for egl-10 cDNA).

FIG. 2B shows the positions of egl-10 introns and exons and the positions of egl-10 mutations therein.

FIG. 2C is Northern Blot analysis with egl-10 cDNA.

FIG. 2D is the sequence of egl-10 mutations.

FIG. 3B shows the sequences of RGS regions of homology (SEQ ID NOS: 1, 6–14, 28–32, 30–32, and 316–39. The RGS-3–4 sequences are isolated from the rest).

FIG. 3C is a comparison of the EGL-10 amino acid sequence and the human RGS7 sequence (SEQ ID NOS 27 and 40).

FIG. 5 shows the partial DNA sequences from the rat rgs genes, referred to as RGS5 1–7 sequences (SEQ ID NOS: 15–23).

Figure 6A:
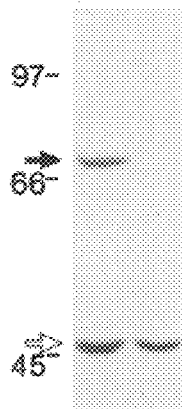
Figure 6B:
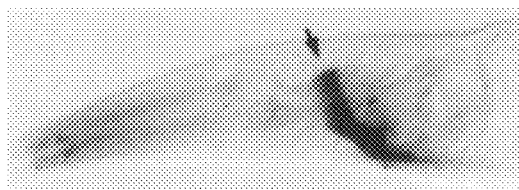
Figure 6C:
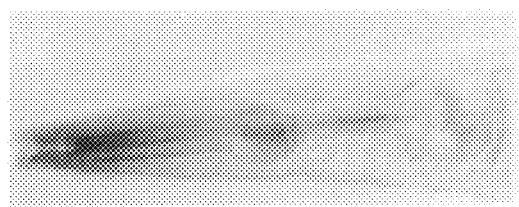
Figure 6D:
Figure 6E:
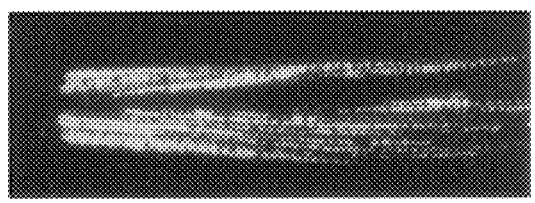
Figure 6F:
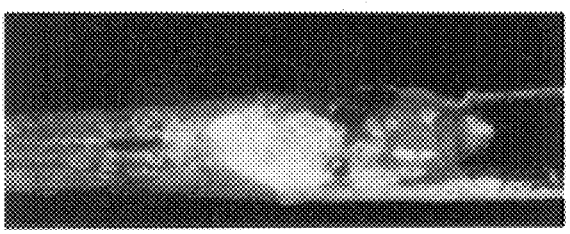
Figure 6G:
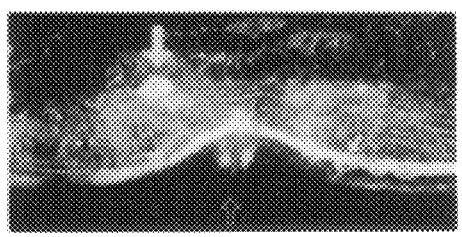

FIG. 6A–6G show EGL-10 protein expression. FIG. 6A shows western blot analysis of protein extracts from wild-type and egl-10(md176) worms probed with the affinity purified anti-EGL-10 polyclonal antibodies. The filled arrow indicates the position of the EGL-10 protein detected in wild-type but not in egl-10 mutant extracts. The open arrow indicates the 47 kD protein that cross-react with the EGL-10 antibodies but was not a product of the EGL-10 gene. The positions of molecular weight markers are indicated, with their sizes in kD. FIG. 6B shows anti-EGL-10 antibody staining of the head of a wild-type adult hermaphrodite. The dark immunoperoxidase stain labeled the neural processes of the nerve ring (arrow). FIG. 6C shows anti-EGL-10 antibody staining of the head of an egl-10(md176) adult hermaphrodite, prepared in parallel to the preparation on FIG. 6B and lacking any specific staining. FIG. 6D shows anti-EGL-10 immunofluorescence staining in the mid-body region of a wild-type adult. The fluorescence here and in panels E–G appears white on a black background, the reverse of the staining in FIG. 6B and 6C. The arrow points to the brightly stained ventral cord neural processes. Body-wall muscle cells on either side of the ventral cord contained brightly stained spots arranged in linear arrays. Body-wall muscles throughout the animal showed similar staining. FIG. 6E shows fluorescence in the head of a transgenic adult carrying a fusion of the egl-10 promoter and N-terminal coding sequences to the green fluorescent protein (GFP) gene. The fusion protein is localized in spots within the body-wall muscles similar to those seen in FIG. 6D. GFP fluorescence was also present in neural processes and cell bodies out of the plane of focus. FIG. 6F shows anti-EGL-10 antibody staining in the head of a transgenic worm carrying the nIs51 multicopy array of wild-type egl-10 genes. FIG. 6G shows anti-EGL-10 antibody staining in the vulva region of nIs51 worms. The open arrow points to the vulva. The large filled arrow indicates the HSN neuron. The small filled arrow points to the ventral cord and associated neural cell bodies.

FIG. 7 shows the human rgs2 cDNA sequence (SEQ ID NO:41).

I. EGL-10 identifies a new family of heterotrimeric G-protein pathway associated proteins which are regulators of G-protein signalling (RGS's)

A. Characteristics of egl-10.

1. Phenotypes conferred by mutation of the egl-10 gene.

The phenotypes conferred by mutations in egl-10 have been further characterized. As previously described, egl-10 loss-of-function mutants fail to lay eggs and have sluggish locomotory behavior (C. Trent, et al. (1983) Genetics 104:619–647)). We have now discovered that the overexpression of egl-10 produces the opposite effects: hyperactive egg-laying and locomotion. More generally, we have discovered that the rates of egg-laying and locomotory behaviors are proportional to the number of functional copies of egl-10.

The phenotypes conferred by mutations in egl-10 are strikingly similar to those conferred by mutations in goa-1 (J. E. Mendel, et al. (1995) Science 267:1652–5); L. Ségalat, et al. (1995) Science 267:1648–52). However, these phenotypes are reversed relative to the level of gene function: mutations of egl-10 which enhance gene function increase the rate of various behaviors whereas those mutations that reduce gene function decrease the rates of these behaviors. By contrast, mutations goa-1 which reduce function increase the rate of behaviors, whereas overexpression decreases the rate of the behaviors. The occurrence of such a similar constellation of phenotypes strongly suggests that the functions of EGL-10 and GOA-1 proteins have related functions, components of the same or parallel genetic pathway. Since GOA-1 is the nematode homolog of the heterotrimeric G-protein, Gαo, it is thus likely that EGL-10 plays a role in one or more heterotrimeric G-protein regulatory pathways which contains Gαo.

We have further discovered that loss of function mutations in egl-10 confer resistance to drugs that effect C. elegans by acting as inhibitors of acetylcholinesterase (AChE). Other mutations that confer resistance to AChE inhibitors have been shown to reduce the synthesis and packaging of the neurotransmitter acetylcholine (ACh) or to reduce the function of genes that encode proteins that comprise the biochemical machinery responsible for neurotransmitter release (M. Nguyen, A. Alfonso, C. D. Johnson and J. B. Rand (1995) Genetics 140:527–35). This result indicates that EGL-10, and presumably its associated G-protein coupled pathways, function to modulate the release of acetylcholine in C. elgans and may be involved in the release of other neurotransmitters as well.

Figure 1A:
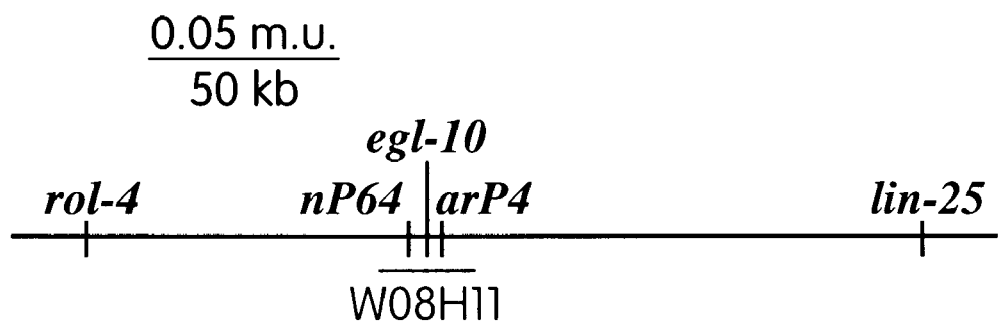
FIG. 1A is the genetic map of region of *C. elegans* chromosome V that contains the gene egl-10.
Figure 1B:
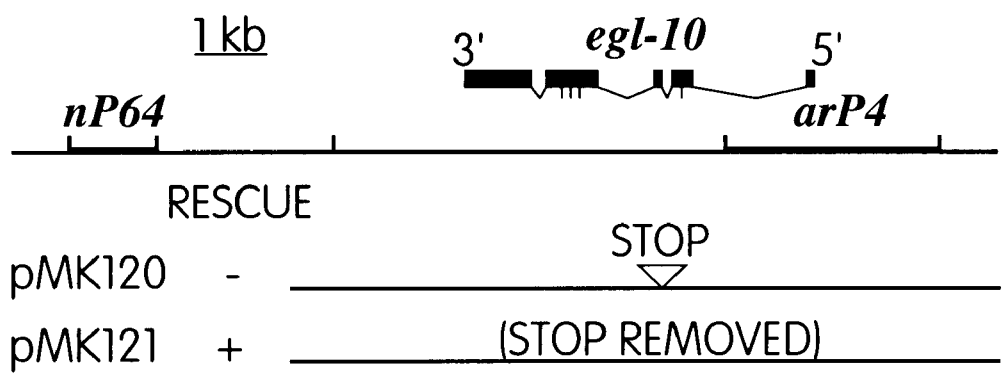
FIG. 1B is a physical map of the egl-10 region of the *C. elegans* genome.

2. The cloning and sequencing of the egl-10 gene.

egl-10 had been previously mapped between rol-4 and lin-25 on chromosome V. Additional mapping, using RFLP markers, placed egl-10 within ~15 Kb of DNA, contained entirely on a single cosmid clone (FIG. 1A). Germline transformation with DNA from a subclone from the region rescues the phenotype conferred by a mutation that reduces egl-10 function. Furthermore, the rescue is blocked by insertion of a synthetic oligonucleotide which interrupts an open reading frame, located entirely within the rescuing fragment, with a stop codon (FIG. 1B). The open reading thus very likely encodes the EGL-10 protein.

The fragment used for transformation rescue was used to screen several C. elegans cDNA libraries. The longest cDNA obtained (3.2 kb) was sequenced on both strands. The cDNA was judged to be full length since it contains a sequence matching the C. elegans trans-spliced-leader SL1 (M. Krause and D. Hirsh (1987) Cell 49:753–61). The regions of the genomic clone to which this cDNA hybridized were sequenced on one strand. The egl-10 genomic structure was deduced by comparing the cDNA and genomic sequences. The 3169 nucleotide long sequence obtained from the cDNA and the 555 amino acid long predicted amino acid sequence of the putative EGL-10 protein are shown in FIG. 2A. The organization of exons and introns within genomic DNA are shown in FIG. 2B. Northern blot analysis (FIG. 2C) showed the presence of a single mRNA species at ~3.2 kB.

We sequenced the putative egl-10 genomic cDNA obtained from a collection of independently isolated egl-10 mutations. Nine mutations induced by chemical mutagenesis were shown to contain point mutations within the gene. Six of the mutations created new stop codons leading to truncated proteins; the other three mutations produced amino acid sequence changes (FIG. 2D). Five spontaneous egl-10 mutations, isolated from a genetically unstable strain of C. elegans, were shown to contain either an insertion of the transposon Tc1 or a rearrangement (FIG. 2D). Locations of these mutations within the gene are shown in FIGS. 2A and 2B. The observation that many egl-10 mutations have detectable defects in a putative egl-10 cDNA is considered proof that this cDNA encodes the EGL-10 gene product.

B. egl-10 is a member of a new gene family—rgs family.

Figure 3A:
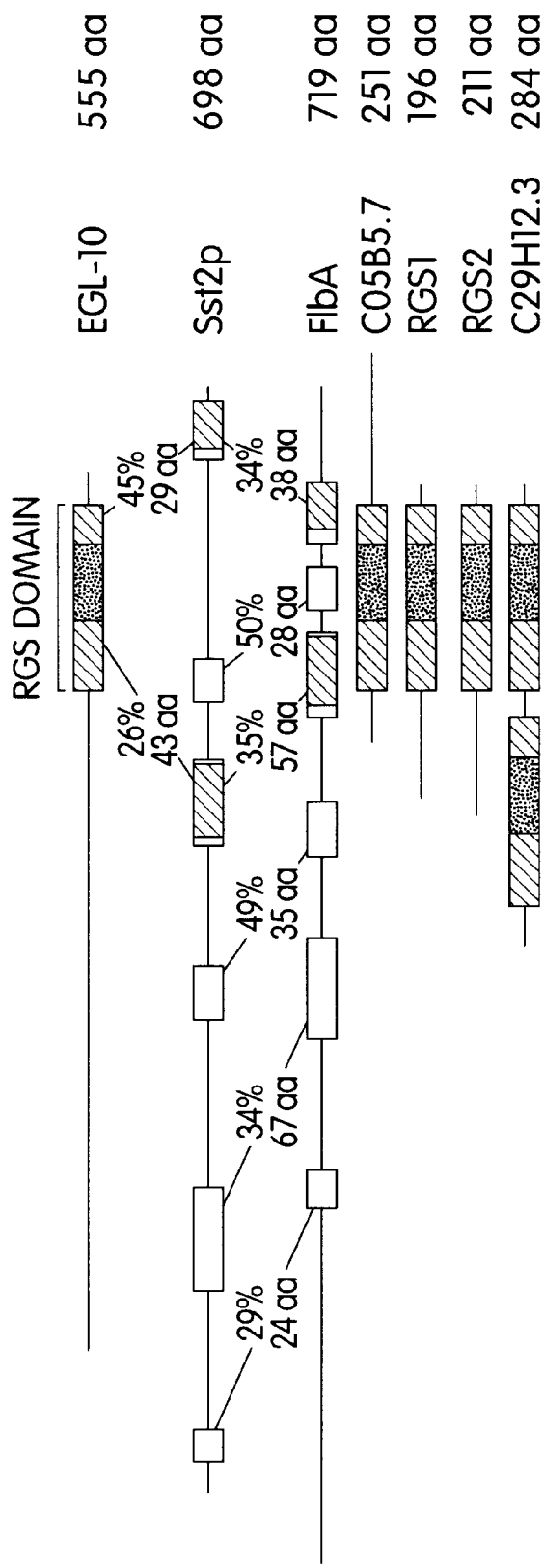
FIG. 3A is a diagram of EGL-10 and structurally related proteins showing amino acid sequences in conserved domains.

The egl-10 gene consists largely of novel sequences. However, a search of protein sequence databases indicated that the gene encodes a 119 amino acid domain (FIG. 3A) that is also present in the predicted amino acid sequences of two small human genes, known as BL34/IR20 and GOS-8. The functions of BL34/1R20 and GOS-8 were previously completely unknown, and these genes were identified only as sequences whose expression is increased in B lymphocytes stimulated with phorbol esters. In addition, a conceptual gene of unknown function, called C05B5.7, identified by the C. elegans genome sequencing project, also contains this conserved domain. Thus, EGL-10 appears to identify a family of proteins with multiple members in the same species and homologs in related species. By using degenerate probes from the conserved domain (in EGL-10, BL34/1R20, GOS-8, and C05B5.7) and PCR, we isolated 9 novel sequences that contain the conserved domain from rat brain cDNA (labelled as rat gene fragments 3 through 11; FIG. 3B). The rat gene fragments isolated using this method are called rgss-1 through rgss-9 for regulator G-protein signalling similarity. It appears that there exists a substantial number of genes in mammals that are members of the rgs family.

We also observed weak sequence similarities between portions of the conserved domain in egl-10 and regions of the sst-2 gene of the yeast *Saccharomyces cerevisiae* and the flbA gene is the fungus *Aspergillis nidulans*. The function of the SST-2 protein appears to involve one mode of adaptation in the G-protein pathway responsible for transduction of the binding of the yeast mating factors a and α to their respective 7-TMRs. Evidence from studies of the sensitivity of yeast Gα to a specialized form of proteolysis, suggests that SST-2 protein may interact directly with Gα. The functions of FlbA are much less well studied.

II. Methods for identifying new members of the rgs/egl-10 gene family

The region of homology we have identified may be used to obtain additional members of the RGS family. For example, sequences from the genes rgss-1 through rgss-9 were obtained by PCR using degenerate oligonucleotide primers designed to encode the amino acid sequences of EGL-10, 1R20, and BL34 proteins at the positions indicated in FIG. 3B. Two 5' primers pools were used with two 3' primer pools in all four possible combinations. After two rounds of amplification all four primer pairs gave a detectable products of ~240 bp. These products were used to prepare clone libraries, restriction maps were prepared for selected clones from each library, clones with different restriction maps were divided into classes, and then several clones from each restriction map class were sequenced. In total 47 clones were sequenced. Each of the nine rgs genes identified by this approach was isolated at least twice. As a result, we conclude that it is likely that we have identified nearly all the rgs genes that can be amplified from rat brain cDNA using these primer pairs.

Figure 4:
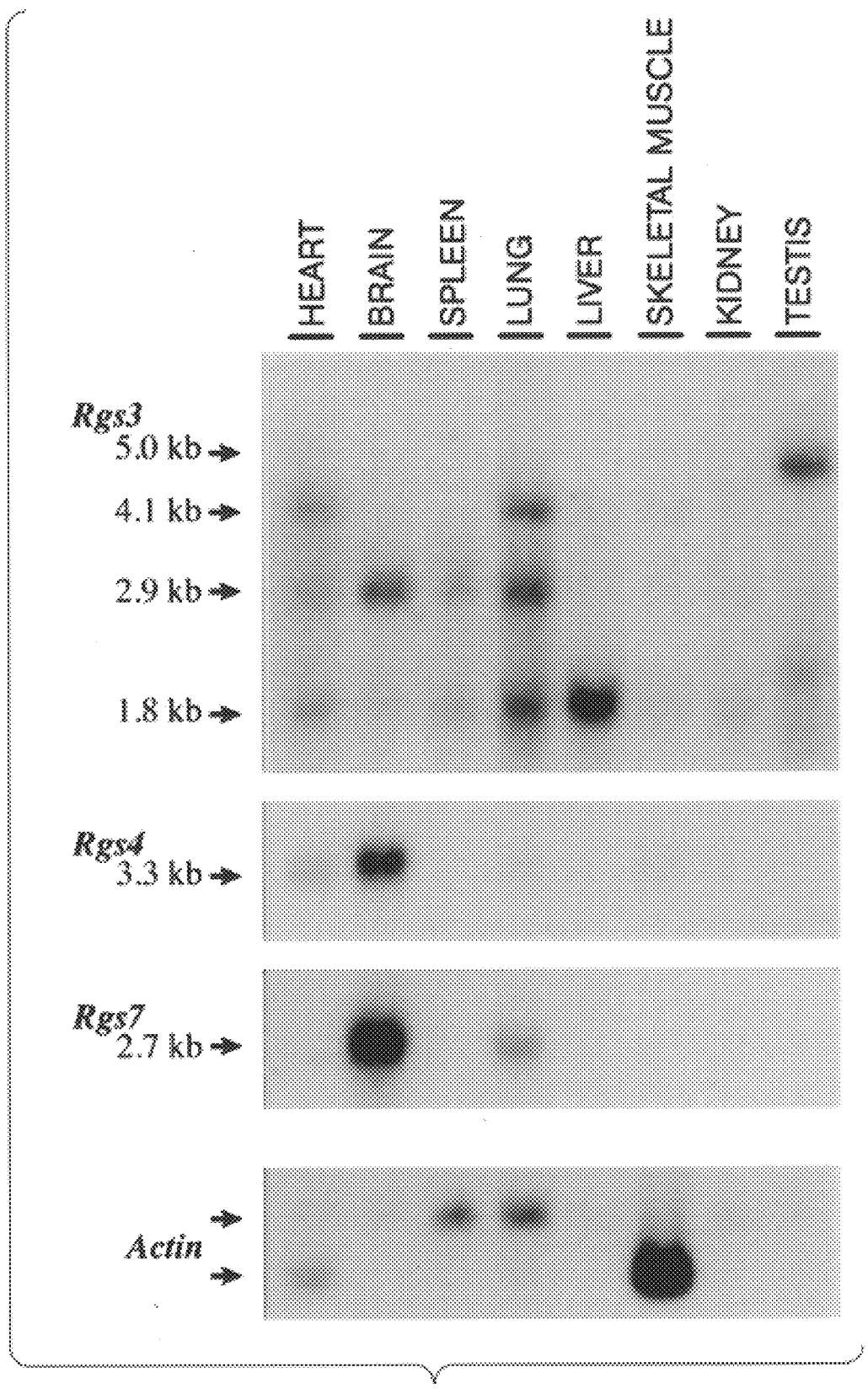
FIG. 4 is a photograph of a Northern blot showing distribution of egl-10 homolog mRNAs in various rat tissues.

At least some of the rgs sequences are expressed in a wide variety of mammalian tissues, as demonstrated by Northern blotting (FIG. 4). Additional G-protein signalling genes may be identified by using the same primer pairs with cDNA from other rat tissues, with human cDNAs or with cDNAs from other species. In addition, additional rgs genes may be identified using alternate primers, based on different amino acid sequences that are conserved not only in the EGL-10, BL34 and 1R20 proteins, but also in the conceptual protein encoded by C05B5.7, in SST2 and FlbA and in the proteins encoded by the rgs genes described herein.

III. The functional characterization of new rgs/RGS family members

A. General considerations.

The function of newly discovered rgs genes can be determined by analyzing:

i) the effects of RGS proteins in vivo and in vitro, ii) the effects of antibodies specific to RGS proteins, or iii) the effects of antisense rgs oligonucleotides in well characterized assay systems that measure functions of mammalian heterotrimeric G-protein coupled pathways.

Relevant assays for RGS activity include systems based on responses of intact cells or cell lines to ligands that bind to 7-TMRs, systems based on responses of premeabilized cells and cell fragments to direct or indirect activation of G-proteins and in vitro systems that measure biochemical parameters indicative of the functioning of G-protein pathway components or an interaction between G-protein pathway components. The G-protein pathway components whose functions or interactions are to be measured can be produced either through the normal expression of endogenous genes, through induced expression of endogenous genes, through expression of genes introduced, for example, by transfection with a virus that carries the gene or a cDNA for the gene of interest or by microinjection of cDNAs, or by the direct addition of proteins (either recombinant or purified from a relevant tissue) to an in vitro assay system.

B. Specific assay systems which may be employed to detect and screen new RGS genes and polypeptides.

Specific assay systems, including those which are relevant to the pathophysiology of human disease and/or are useful for the discovery and characterization of new targets for human therapeutics are as follows:

1. Assays based on natural responses of intact cells.

Many mammalian cells, for example cardiac myocytes, other smooth muscle cells, neutrophils, mast cells and other classes of myeloid cells and insulin secreting β cells of the pancreas have readily detected responses mediated by heterotrimeric G-protein dependent pathways. To determine if a particular RGS protein is involved in such a pathway, one may compare the response of normal cells to the response which is obtained in cells transfected or transiently transformed by the rgs gene. Transformation may be done with the RGS cDNA under the appropriate promotor or with a construct designed to overexpress antisense oligonucleotides to the rgs mRNA.

For example, we could express an rgs gene or antisense oligonucleotides to an rgs mRNA in mammalian cardiac myocytes as described, for example, by Ramirez et al. (M. T. Ramirez, G. R. Post, P. V. Sulakhe and J. H. Brown (1995) J. Biol. Chem. 270:8446–51). Cardiac myocytes system respond to a variety of ligands, for example α- and β-adrenergic agonists and muscarinic agonists, by altering membrane conductances, including conductances to $Cl^-$, $K^+$ and $Ca^{2+}$. These effects are mediated by G-proteins through a web of both second messenger mediated and membrane delimited effects and are readily measured with a variety of well known electrophysiological technologies (for example: T. C. Hwang, M. Horie, A. C. Nairn and D. C. Gadsby (1992) J. Gen. Physiol. 99:465–89.). We would compare the response of normal myocytes to cells that overexpress a particular rgs gene or antisense oligonucleotides to a particular rgs mRNA. If no difference was observed, we would conclude that the particular RGS protein played no detectable role in cardiac myocyte physiology. On the other hand, if alterations in membrane currents were observed we would dissect the altered response using pharmacology, permeabilized cell systems and reconstitute G-protein pathways systems to determine the site of action of the RGS protein. One may use this system for specific screens to identify and test compounds that mimic or block the function of the RGS protein.

2. Assays based on expression of cloned genes in particular cells or cell lines.

The involvement of a RGS protein in some known functions and interactions between components of heterotrimeric G-protein pathways can be efficiently assessed in model systems designed for easy and efficient overexpression of cloned genes. One well developed system uses COS-7 cells (monkey kidney cells which possess the ability to replicate SV-40 origin-containing plasmids) as a host for the expression of cloned genes and cDNAs (D. Q. Wu, C. H. Lee, S. G. Rhee and M. I. Simon (1992) J. Biol. Chem. 267:1811–7). Recently, for example, overexpression of G-protein pathway genes in COS-7 cells was used to determine the capability of two forms of interleukin-8 receptor to activate the 5 different Gα subunits of the Gq family by measuring subsequent effects on the activity of two alternate types of PI-PLCβ, measured by quantified the formation of [H³]IP3 in cells prelabelled with radioactive inositol (D. Wu, G. J. LaRosa and M. I. Simon (1993) Science 262:101–3). Similarly co-expression in COS-7 cells has been used to quantitate the effects of proteins that inhibit signalling by activated G-proteins (W. J. Koch, B. E. Hawes, J. Inglese, L. M. Luttrell and R. J. Lefkowitz (1994) J. Biol. Chem. 269:6193–7).

A useful alternative to cells lines, more amenable to the study of membrane delimited activation of ion channels involves the transient production of proteins following injection of mRNAs into Xenopus oocytes (E. Reuveny, P. A. Slesinger, J. Inglese, J. M. Morales, J. A. Iniguez-Lluhi, R. J. Lefkowitz, H. A. Bourne, Y. N. Jan and L. Y. Jan (1994) Nature 370:143–6). For example, the coexpression of two 7-TMRs (serotonin type 1C receptor and thyrotropin releasing hormone receptor) may be coupled with overexpression of one of seven alternate Gα subunits and with one of two alternate PI-PLCβs or adenylyl cyclase and the cystic fibrosis transmembrane conductance regulator (CFTR) (M. W. Quick, M. I. Simon, N. Davidson, H. A. Lester and A. M. Aragay (1994) J. Biol. Chem. 269:30164–72). Combined with expression of antisense oligonucleotides designed to block endogenous pathways, these systems can be engineered to measure specific interactions between 7-TMRS, G subunits, effectors, various inhibitors as well as components controlled by effectors. To determine the effect of an RGS protein one may compare the effect in transfected COS-7 cells or Xenopus oocytes with and without cotransfection with the rgs gene or cDNA, one may also transfect an rgs gene construct designed to overexpress antisense oligonucleotides to endogenous rgs mRNAs.

If a RGS protein-dependent alteration of a G-protein dependent response is observed, one may utilize pharmacological tools and reconstitute G-protein pathways systems to determine the site of action of the RGS protein. From these experiments, a specific screen for identifying and testing compounds that mimic or block the function of the RGS protein may be developed.

3. Assays utilizing premeabilized cells.

The role of RGS proteins in intracellular events such as membrane trafficking or secretion can be studied in systems utilizing permeabilized cells, such as mast cells (T. H. Lillie and B. D. Gomperts (1993) Biochem. J. 290:389–94), chromaffin cells of the adrenal medulla (N. Vitale, D. Aunis and M. F. Bader (1994) Cell. Mol. Biol. 40:707–15) or more highly purified systems derived from these cells (J. S. Walent, B. W. Porter and T. F. J. Martin (1992) Cell 70:765–775). The determine the effects of RGS proteins one may compare the extent and kinetics of GTP or γS-GTP induced secretion in the presence and absence of excess RGS protein or antibodies specific to RGS proteins.

If an RGS protein-dependent alteration of membrane trafficking or secretion is observed, further experiments may be used to explore the specificity and generality of this action and to determine the precise site of action of the RGS protein. From these experiments, a specific screen for identifying and testing compounds that mimic or block the function of the RGS protein can be constructed.

4. Assays utilizing reconstituted G-protein pathways.

The ability to assess specific protein-protein interactions between specific components that function within G-protein pathways may be employed to assign RGS functions. These assays generally use recombinant proteins purified from an efficient expression systems, most commonly, i) insect Sf9 cells infected with recombinant baculovirus or ii) E. coli. Specific interactions which form part of G-protein pathways are then reconstituted with purified or partially purified proteins. The effects of RGS proteins on such systems can be easily assessed by comparing assays in the presence and absence of excess RGS protein or antibodies specific to RGS proteins. From these experiments, specific screens for identifying and testing compounds that mimic or block the function of the RGS protein can be developed.

Uses

RGS DNA, polypeptides, and antibodies have many uses. The following are examples and are not meant to be limiting. The RGS encoding DNA and RGS polypeptides may be used to regulate G-protein signalling and to screen for compounds which regulate G-protein signalling. For example, RGS polypeptides which increase secretion may be used industrially to increase the secretion into the media of commercially useful polypeptides. Once proteins are secreted, they may be more readily harvested. One method of increasing such secretion involves the construction of a transformed host cell which synthesizes both the RGS polypeptide and the commercially important protein to be secreted (e.g, TPA). RGS proteins, DNA, and antibodies may also be used in the diagnosis and treatment of disease. For example, regulation of G-protein signalling may be used to improve the outcome of patients with a wide variety of G-protein related diseases and disorders including, but not limited to: diabetes, hyperplasia, psychiatric disorders, cardiovascular disease, McCune-Albright Syndrome, and Albright hereditary osteopathy.

IV. Deposit Information

Genebank accession numbers for the sequences provided herein are as follows: The worm sequence, egl-10; has number U32326. The rgs sequence fragments isolated from the rat as follows: rgs5, U32434; rgs1, U32327; rgs6, U32435; rgs7, U32436; rat rgs2, U32328; rgs3, U32432; rgs4, U32433; rgs8, U32437; rgs8, U32438. Accession numbers for representative expressed sequence tags from human rgs genes are: RGS-1, R12757, F07186; RGS6, D31257, R35272; RGS10, R35472, T57943; RGS13, T94013; RGS11, R11933; RGS12, T92100. The human RS7 accession number is 442439.

V. Examples

A. Characteristics of egl-10.

1. Nematode strains.

Nematode strains were maintained and grown at 20° C. as described by Brenner (Brenner, (1974) Genetics 77:71–94). Genetic nomenclature follows standard conventions (Horvitz et al., (1979) Mol. Gen. Genet. 175:129–33). The following mutations were used: goa-1(n363, n1134) (Ségalat et al., (1995) Science 267:1648–51), arDf1 (Tuck and Greenwald, (1995) Genes & Development 9:341–57), egl-10 alleles (Trent et al., (1983) Genetics 104:619–47); Desai and Horvitz, (1989) Genetics 121:703–21), nIs51 (this work), nIs67 (this work). We also used the following marker mutations, described by Wood (Wood, ed. (1988) Cold Spring Harbor, N.Y.: Cold Spring Harbor Laboratory): (LG I), unc-13(e1091); (LGV), unc-42(e270), lin-25(n545), him-5(e1467); (LGX), lin-15(n765).

2. The genetic map position of egl-10.

egl-10 had previously been mapped between rol-4 and lin-25 on chromosome V (Trent et al., (1983) Genetics 104:619–647; Desai and Horvitz, (1989) Genetics 121:703–21). We characterized four Tc1 transposon insertions found in this interval in the Bergerac strain of C.

elgans, but not in the standard Bristol (N2) strain: nP63, nP64, arP4 and arP5 (first identified by Tuck and Greenwald, ((1995) Genes & Development 9:341–57). From heterozygotes of the genotype eg1-10(n692)/rol-4(sc8) nP63 nP64 arP4 arP5 lin-25(n545) him-5(e1467), Rol non-Lin recombinants were selected. Strains homozygous for the recombinant chromosomes were assayed for the Egl-10 phenotypes (sluggish movement and defective egg-laying), and for the presence of each of the transposons by probing Southern blots of genomic DNA with appropriate genomic clones. Nine recombination breakpoints were thus found to distribute as follows: rol-4 (2/9) nP63 (0/9) nP64 (1/9) egl-10 (1/9) arP4 (1/9) arP5 (4/9) lin-25. These data place the egl-10 gene in the interval between nP64 and arP4 (FIG. 1A).

3. goa-1; egl-10 double mutants.

goa-1; egl-10 strains were constructed by using the unc-13(e1091) mutation, which lies within 80 kb of the goa-1 gene (Maruyama and Brenner, (1991) Proc. Nat'l. Acad. Sci. U.S.A. 88:5729–33), to balance the goa-1 mutations. unc-13/+; egl-10/+ males were mated to goa-1 hermaphrodites and hermaphrodite cross progeny were placed individually on separate plates. unc-13/goa-1; egl-10/+ animals were recognized as segregating ¼ Unc (uncoordinated) and ~¼ Egl (egg-laying defective) progeny. Among these progeny, Egl non-Unc animals were picked to separate plates, and were judged to be of genotype goa-1/unc-13; egl-10 if they segregated ¼ Unc and >¾ Egl progeny. Non-Unc progeny were picked individually to separate plates, and goa-1; egl-10 animals were recognized as never segregating Unc progeny. The following double mutant strains were constructed: MT8589 goa-1(n1134); egl-10(n990), MT8593 goa-1(n363); egl-10(n990), MT8641 goa-1(n363); egl-10 (n944), MT8587 goa-1(n1134); egl-10(n944), goa-1(n363); egl-10(md176).

Animals with reduction of function mutations in both goa-1 and egl-10 display a behavioral phenotype that is very similar to that of strains with mutations in goa-1 alone, i.e. the animals have hyperactive locomotion and precocious egg-laying. This observation implies that EGL-10 protein acts either before or at the same step in the G-protein regulatory pathway as the GOA protein, Gαo.

4. Germline transformation and chromosomal integration of egl-10 transgenes.

Germline transformation (Mello et al., (1991) Embo. J. 10:3959–70) was performed by coinjecting the experimental DNA (80 μg/ml) and the lin-15 rescuing plasmid pL15EK (Clark et al., (1994) Genetics 137, 987–97) into animals carrying the lin-15(n765) marker mutation. Transgenic animals typically carry coinjected DNAs as semistable extrachromosomal arrays (Mello et al., (1991) Embo. J. 10:3959–70) and are identified by rescue of the temperature sensitive multivulva phenotype conferred by the lin-15 (n765) mutation. For egl-10 rescue experiments, animals of the genotype egl-10(n692); lin-15(n765) were injected, and transgenic lines were considered rescued if >90% of the non-multivulva animals did not show the egg laying defective phenotype conferred by the egl-10(n692) mutation. Plasmid pMK120 contains a 15 kb SmaI-FspI fragment of cosmid W08H11, containing the entire egl-10 gene, into which the self-annealed oligonucleotide 5'-GTGCTAGCACTGCA-3' (SEQ ID NO: 35) was inserted at the unique PstI site, thus disrupting the open reading frame of the fourth egl-10 exon. pMK121 was generated by digesting pMK120 with PstI and ligating, thus precisely removing the oligonucleotide and restoring the egl-10 open reading frame. egl-10 was rescued in all 13 transgenic lines carrying pMK121 that were generated, while 0/17 pMK120 lines showed egl-10 rescue of even a single animal (FIG. 1B).

5. egl-10 cDNAs and the egl-10 genomic structure.

An 8.5 kb ApaI-MscI fragment, encompassing the middle half of the egl-10 rescuing genomic clone pMK120, was used to screen $3.7 \times 10^6$ plaques from four different C. elegans cDNA libraries (Barstead and Waterston, (1989) J. Biol. Chem. 264:10177–85; Maruyama and Brenner, (1992) Gene 120:135–41.; Okkema and Fire, (1994) Development 120:2175–86.). Thirteen egl-10 cDNAs were isolated, the longest of which was 3.2 kb. This cDNA was completely sequenced on both strands using an ABI 373A DNA sequencer (Applied Biosystems, Inc.). The sequence data was compiled on a Sun workstation running software as described by Dear and Staden (Dear and Staden, (1991) Nucleic Acids Research 19:3907–11) and displayed in FIG. 2A. The regions of the pMK120 genomic clone to which this cDNA hybridized were also sequenced on one strand, and the egl-10 genomic structure was deduced by comparing the cDNA and genomic sequences (FIG. 2B). The 3.2 kb cDNA was judged to be full length since it contains a sequence matching the C. elegans trans-spliced leader SL1 (Krause and Hirsh, (1987) Cell 49: 753–61) at its 5' end, a poly(A) tract at its 3' end (although it lacks a consensus poly(A) addition signal), and matches the length of the 3.2 kb RNA detected by Northern hybridization (FIG. 2C). Other cDNAs were shorter but colinear with the 3.2 kb cDNA clone as judged by restriction mapping and end sequencing.

6. egl-10 mutant DNAs.

egl-10 genomic DNA was PCR amplified from egl-10 mutants in ~1 kb sections using primers designed from the egl-10 genomic sequence. The PCR products were electrophoresed on agarose gels, and the excised PCR fragments were purified from the agarose by treatment with β-agarase (New England Biolabs) and isopropanol precipitation. The purified PCR products were directly sequenced using the primers that were used to amplify them, as well as primers that annealed to internal sites. Any differences from the wild-type sequence were confirmed by reamplification and resequencing of the site in question. In this way the entire egl-10 coding sequence as well as sequence 20 bp into each egl-10 intron was determined for each of ten ethyl methanesulphonate (EMS)-induced egl-10 alleles (Trent et al., (1983) Genetics 104:619–647; Desai and Horvitz, (1989) Genetics 121:703–21), as well as for the spontaneous allele md1006. The alterations discovered are listed in FIG. 2D. One EMS-induced egl-10 allele, n953, appeared to contain no alterations from wild type in the region sequenced, but may contain alterations in other parts of the gene. md1006 contains no sequence alterations from wild type other than the insertion of a Tc1 transposon at codon 515.

Genomic DNA from each of five spontaneous egl-10 alleles was analyzed by Southern blotting and probing with clones spanning the egl-10 gene. md1006 contains a 1.6 kb insert relative to wild type which was shown to be a Tc1 transposon insertion by PCR amplification using primers that anneal to the Tc1 ends with primers that anneal to egl-10 sequences flanking the insertion site, and by further sequencing these PCR products. The four other spontaneous alleles each contain multiple restriction map abnormalities spanning the entire egl-10 locus, and each failed to give PCR amplification products using one or more primer pairs from the egl-10 gene. None of these alleles appear to be due to a simple insertion or deletion, and we suspect more complex rearrangements may have occurred.

7. Localization of EGL-10 protein in neural processes and subcellular regions of body wall muscle cells.

We raised polyclonal antibodies against recombinant EGL-10 protein. When affinity-purified, these antibodies recognized two major proteins on western blots of total *C. elegans* proteins (FIG. 6A). The larger of these proteins is the product of the egl-10 gene, since this protein was absent from extracts of the egl-10 null mutant md1176 (FIG. 6A), as well as from extracts of 12 other egl-10 mutants. This larger protein was detected at a reduced abundance in the weak egl-10 mutant n480 and was present at normal abundance in egl-10 (n1125) animals, which carry a missense mutation that alters amino acid 446. The 47 kD protein recognized by the anti-EGL-10 antibodies is not affected by egl-10 mutations and thus is not encoded by the egl-10 gene (FIG. 6A).

We stained wild-type and egl-10 mutant worms with the affinity-purified anti-EGL-10 antibodies. We observed staining in the nerve ring (FIG. 6B), ventral nerve cord (FIG. 6D), and dorsal nerve cord (not shown) of wild-type animals, but saw no neural staining in egl-10 mutants (FIG. 6C). The stained structures consisted of bundles of neural processed and were at the locations of the majority of the chemical synapses in the animal (White et al., Phil. Trans. R. Soc. Lond. B 314:1–340, 1986). In neurons EGL-10 protein appeared to be localized exclusively to processes; no staining was seen in the neural cell bodies of wild-type animals. Animals at all stages of development from first-stage larvae to adults showed similar staining of neural processes. The localization of EGL-10 protein to structures in which chemical synapses are made is consistent with a role for EGL-10 in intercellular signalling.

We also used the EGL-10 antibodies to stain worms that overexpress EGL-10 from a multicopy array of egl-10 transgenes (FIGS. 6F, 6G). EGL-10 was detected in neural cell bodies as well as neural processes of these animals, either because overexpression raised the level of EGL-10 protein in cell bodies above the threshold of detection or because overexpression of EGL-10 exceeded the capacity of neurons to localize the protein to processes. FIG. 6F shows that a large number of neurons in the major ganglia of the head region expressed EGL-10. In addition, our examination of the ventral cord neurons, lateral neurons, and tail ganglia suggested that most if not all neurons in *C. elegans* expressed EGL-10. In particular, the HSN motor neurons, which control egg-laying behavior and appear to be functionally defective in egl-10 mutants, expressed EGL-10 (FIG. 6F).

A second staining pattern present in wild-type animals consisted of spots arranged in linear arrays within the body-wall muscle cells (FIG. 6D). Although this staining was not absent from egl-10 null mutants, we nevertheless believe that the EGL-10 protein is localized to these muscle structures, since the muscle stain was more intense in EGL-10 overexpressing animals and was reproduced by egl-10::gfp transgenes (see below). The residual antibody stain seen in the muscles of egl-10 mutants may have been caused by the presence of a cross-reactive protein (perhaps the 45 kD protein detected in our western blots) that is colocalized with EGL-10. The body-wall muscles are used in locomotion behavior (Wood et al., *The Nematode Caenorhabditis elegans*, Cold Spring Harbor, N.Y., Cold Spring Harbor Laboratory Press, 1988), the frequency of which is controlled by egl-10. Every body wall muscle cell stained, but no staining was detected in other types of muscle cells, even in animals overexpressing EGL-10. The body-wall muscle stain superimposed on structures visible in Nomarski optics called dense bodies, which function as attachment sites between the body-wall muscles and the cuticle that surrounds them (Wood et al., supra). Each dense body is flanked by membranes of the sarcoplasmic reticulum, and our observations at the light microscope level cannot distinguish between localization of the stain to the dense bodies or to the sarcoplasmic reticulum. The significance of the localization of EGL-10 to these structure is unclear.

Transgenic animals carrying fusions of the egl-10 promoter and N-terminal coding sequences to the fluorescent reporter protein GFP (Chalfie et al., Science 263:802–805, 1994) showed GFP fluorescence in body-wall muscle cells in the same pattern seen in animals stained with the EGL-10 antibody (FIG. 6E). These experiments demonstrated that the N-terminal 122 amino acids of EGL-10, when fused to GFP, were sufficient to localize the fusion protein to the dense body-sarcoplasmic reticulum-like structures. The EGL-10::GFP fusion proteins were also expressed in neurons but, like overexpressed full-length EGL-10 protein, were not tightly localized to processes, preventing us from identifying the regions of EGL-10 responsible for localization of EGL-10 to neural process.

8. EGL-10 is similar to Sst2p, a negative regulator of G protein signalling in yeast.

Figure 3B:
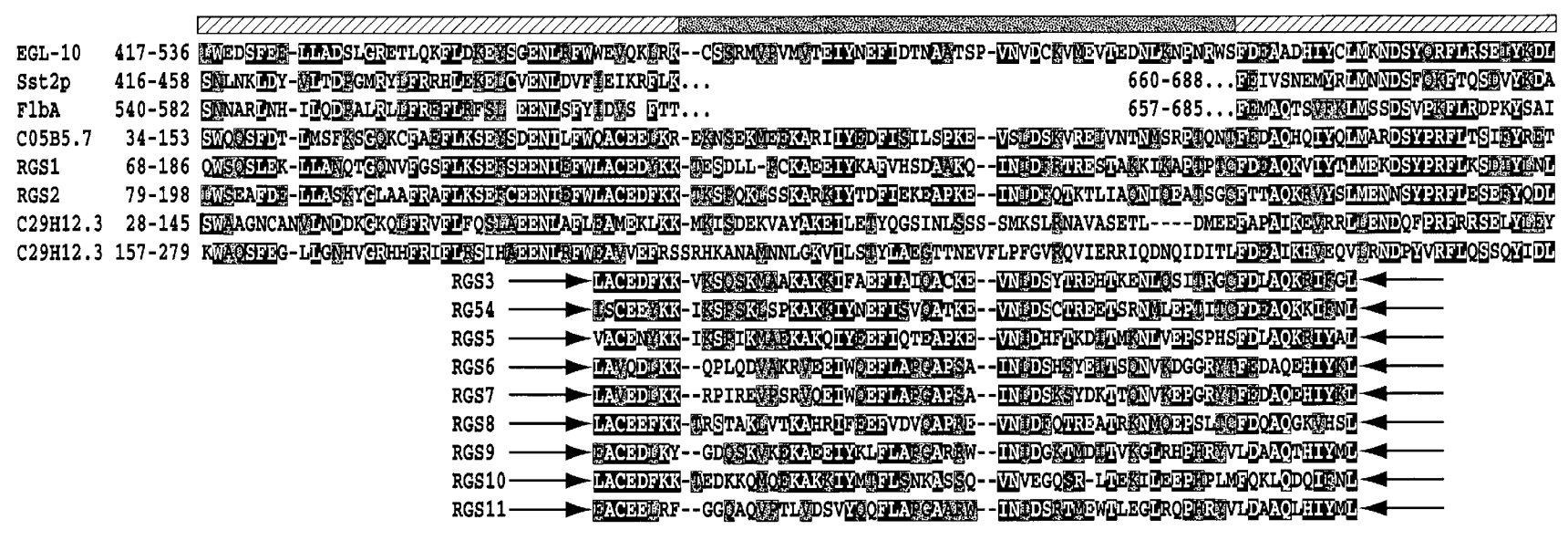

The 555 amino acid EGL-10 protein contains a 120-amino acid region near its carboxy-terminus with similarity to several proteins in the sequence databases (FIG. 3A). The similarities with the *C. elegans* C05B5.7 protein and the BL34/IR20 and GOS8 proteins extend across the entire 120-amino acid region; this region is 34–55% identical in pairwise comparisons among EGL-10 and these other proteins. An additional *C. elegans* protein, C29H12.3, consists almost entirely of two highly diverged repeats of this domain. The first 43 and last 29 amino acids of the conserved 120-amino acid region are similar to sequences found in the yeast protein Sst2P and the Aspergillus nidulans protein FlbA. Sst2p and FlbA are 30% identical to each other over their entire lengths and show higher conservation in several short regions (FIG. 3A); it is two of these more highly conserved regions that show similarity to the conserved domain found in EGL-10, C05B5.7, BL34/IR20, GOS8 and C29H12.3. Alignments of all of these conserved sequences are shown in FIG. 3B. This figure also shows alignments with the sequences of nine additional mammalian EGL-10 protein homologs whose isolation is described below.

The similarity of EGL-10 to Sst2p is of particular interest, since Sst2p functions as a regulator of the G protein-mediated pheromone response pathway in yeast (reviewed by Sprague and Thorner, Cold Spring Harbor, N.Y., Cold Spring Harbor Laboratory Press, pp. 657–744, 1992; and Kurjan, J., Annu. Rev. Genet. 27:147–179, 1993). We concluded from this that EGL-10 and Sst2p are members of an evolutionary conserved family of regulators of G protein signalling.

Little has been previously known about the functions of the other genes that have sequence similarity to egl-10. flbA mutants of *Aspergillus nidulans* are defective in the development of conidiophores, specialized spore-bearing structures (Lee and Adams, Mol. Microbiol. 14:323–334, 1994). The C05B5.7 and C29H12.3 genes were identified by the *C. elegans* genome sequencing project (Wilson et al., supra). BL34/IR20 is a human gene expressed specifically in activated B lymphocytes (Murphy and Norton, Biochem. Biophys. Acta 1049:261–271, 1990; Hong et al., J. Immun. 150:3895–3904, 1993; Newton et al., Biochim. Biophys.

Acta 1216:314–316, 1993). gos8 is a human gene was identified by a clone from a blood monocyte cDNA library (Siderovski et al., DNA Cell. Biol. 13:125–147, 1994).

B. rgs genes: Mammalian homologs of egl-10.

1. Isolation of rgs genes.

Degenerate oligonucleotide primers were designed to encode the amino acid sequences of the EGL-10, 1R20/BL34 and GOS8 proteins at the positions indicated in FIG. 3B. Two 5' primers pools were used with two 3' primer pools in all four possible combinations. The primers contained the base inosine (I) at certain positions to allow promiscuous base pairing.

The 5' primers were:

5E: G(G/A)IGA(G/A)AA(T/C)(A/T/C)TIGA(G/A)TT(T/C)TGG (SEQ ID NO: 2);

5R: G(G/A)IGA(G/A)AA(T/C)(A/T/C)TI(A/C)GITT(T/C)TGG (SEQ ID NO 3).

The 3' primers were:

3T: G(G/A)TAIGA(G/A)T(T/C)ITT(T/C)T(T/C)CAT (SEQ ID NO 4;

3A: G(G/ATA(G/A)CT(G/A)T(T/C)ITT(T/C)T(T/C)CAT (SEQ ID NO 5).

Amplification conditions were optimized by using *C. elegans* genomic DNA as a template and varying the annealing temperature while holding all other conditions fixed. Conditions were thus chosen which amplified the egl-10 gene efficiently while allowing the amplification of only a small number of other *C. elegans* genomic sequences. Amplification reactions for rat brain cDNA were carried out in 50 μl containing 10 mM Tris-HCl (pH 8.3), 50 mM KCl, 1.5 mM MgC12, 0.001% gelatin, 200 μM each of dATP, dCTP, dGTP, and dTTP, 1 U Taq polymerase, 2 μM each PCR primer pool, and 1.5 ng rat brain cDNA as a template (purchased from Clonetech). The optimized reaction conditions were as follows: initial denaturation at 95° C. for 3 min., followed by 40 cycles of 40° C. for 1 min., 72° C. for 2 min., 94° C. for 45 sec., and a final incubation of 72° C. for 5 min. After this initial amplification some primer pairs gave detectable products of ~240 bp. 2 μl of each initial amplification reaction was used as a template for further 40 cycle amplification reactions under the same conditions; all primer pairs gave a detectable ~240 bp product after the second round of amplification. The ~240 bp PCR products were subcloned into EcoRV cut pBluescript (Stratagene) treated with Taq polymerase and dTTP, generating clone libraries for amplifications from each of the four primer pairs. Clones from each library were analyzed as follows: after digestion with the enzymes Stu I, Bgl II, Sty I, Nco I, Pst I, and PpuM I, clones were divided into classes with different restriction maps and several clones from each restriction map class were sequenced using an ABI 373A DNA sequencer (Applied Biosystems, Inc.). A total of 121 clones were restriction mapped, of which 47 were sequenced.

With this approach, we identified nine genes, called rgss-1 through rgss-9 for regulator G-protein signalling similarity genes from rat brain cDNA. Their DNA sequences are displayed in FIG. 3B and their amino acid sequences in FIG. 3B (labelled as rat rgs gene fragments 3 through 11, SEQ ID NOS 15–23). Each of the rat rgs fragments was isolated at least twice. Three of the four primer pairs used identified a gene that was not identified by any of the other primer pairs. Thus we appear to have identified all or nearly all the rgs genes that can be amplified from rat brain cDNA using these primer pairs.

C. Human rgs genes.

We identified additional human genes encoding RGS domains by searching a database of expressed sequence tags. This search identified matches to five previously defined genes (including BL34/IR20 and GOS-8) and apparent human orthologs of the rat rgs1, rgs6, and rgs2 genes—as well as partial sequences of four new genes, which we have named RGS12 through RGS15.

Human RGS2 shares sequence similarity with EGL-10 outside of the RGS domain, unlike other RGS domain proteins for which extended sequences are available. We therefore obtained and determined the sequence of a human rgs2 cDNA (FIG. 7, SEQ ID NO:41). While incomplete at its 5' end, this 1.9 kb cDNA contains a 420-codon open reading frame that encodes a protein with similarity to EGL-10 throughout its length (FIG. 3C; SEQ ID NO:40). The predicted RGS2 protein is 53% identical to EGL-10, with the highest conservation (75% identity) occurring in the N-terminal 174 amino acids of the human RGS2 sequence. The 119-amino acid RGS domain of human RGS2, by contrast, is 46% identical to the corresponding C-terminal region of EGL-10. EGL-10 contains a 79 amino acid serine/alanine rich insertion relative to human RGS2 between these conserved amino- and C-terminal regions. The conserved N-terminal region of EGL-10 functions to localize the protein within muscle cells, and the corresponding region of RGS2 may play a similar role for human RGS2 intracellular localization. It is possible that RGS is the human protein most similar to EGL-10. As a result, human RGS2 is likely to play a functional role analogous to EGL-10 in regulating signaling by $G_0$.

1. Characterization of rat rgs genes.

Southern blots of rat genomic DNA were probed at high stringency with labelled subclones for each of the nine rgs gene PCR fragments. Each probe detected at least one different genomic EcoRI fragment and gave signals of comparable intensity, suggesting that the each rgs PCR product is derived from a single copy gene in the rat genome.

Labelled rgs gene probes were serially hybridized to a Northern blot (purchased from Clonetech) bearing 2 μg of poly(A)+ RNA from each of various rat tissues (allowing time for the radioactive signals to decay between probings). A human β-actin cDNA probe was used to control for loading of RNA. The results indicate that rgs genes are widely and differentially expressed in rat tissues (FIG. 4). This result implies additional rgs genes could be identified by using the same primer pairs with cDNA from other rat tissues, with human cDNAs or with cDNAs from other species. In addition, it is very likely that additional rgs genes could be identified using alternate primers, based on different amino acid sequences that are conserved not only in the EGL-10, BL34/1R20, and GOS8 proteins, but also in the conceptual protein encoded by C05B5.7, the SST2 and FlbA proteins and in the proteins encoded by the rgs genes identified so far.

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
       (A) LENGTH: 123 amino acids
       (B) TYPE: amino acid
       (C) STRANDEDNESS: Not Relevant
       (D) TOPOLOGY: linear (ii) MOLECULE TYPE: protein (xi) SEQUENCE DESCRIPTION: SEQ ID NO:1:

```
Leu Trp Glu Asp Ser Phe Glu Glu Leu Leu Ala Asp Ser Ser Leu Gly
 1               5                  10                  15

Arg Glu Thr Leu Gln Lys Phe Leu Asp Lys Glu Tyr Ser Gly Glu Asn
             20                  25                  30

Leu Arg Phe Trp Trp Glu Val Gln Lys Leu Leu Arg Lys Cys Ser Ser
         35                  40                  45

Arg Arg Met Val Pro Val Met Val Thr Glu Ile Tyr Asn Glu Phe Ile
 50                  55                  60

Asp Thr Asn Ala Ala Thr Ser Pro Val Asn Val Asp Cys Lys Val Met
 65                  70                  75                  80

Glu Val Thr Glu Asp Asn Leu Lys Asn Pro Asn Arg Trp Ser Phe Asp
                 85                  90                  95

Glu Ala Ala Asp His Ile Tyr Cys Leu Met Lys Asn Asp Ser Tyr Gln
                100                 105                 110

Arg Phe Leu Arg Ser Glu Ile Tyr Lys Asp Leu
            115                 120
```

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: Modified-site
       (D) OTHER INFORMATION: N is Inosine.

(xi) SEQUENCE DESCRIPTION: SEQ ID NO:2:

GNNGANAARY TNGANTTRTG G                                           21

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: Modified-site
       (D) OTHER INFORMATION: N is Inosine.

(xi) SEQUENCE DESCRIPTION: SEQ ID NO:3:

```
GNNGANAARY TNSGTTRTGG                                          20
```

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Modified-site
        (D) OTHER INFORMATION: N is Inosine.

(xi) SEQUENCE DESCRIPTION: SEQ ID NO:4:

```
GNTANGANTR NTTRTRCAT                                           19
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: Modified-site
        (D) OTHER INFORMATION: N is Inosine.

(xi) SEQUENCE DESCRIPTION: SEQ ID NO:5:

```
GNTANCTNTR NTTRTRCAT                                           19
```

(2) INFORMATION FOR SEQ ID NO:6:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

```
Ile Ser Cys Glu Glu Tyr Lys Lys Ile Lys Ser Pro Ser Lys Leu Ser
 1               5                  10                  15

Pro Lys Ala Lys Lys Ile Tyr Asn Glu Phe Ile Ser Val Gln Ala Thr
            20                  25                  30

Lys Glu Val Asn Leu Asp Ser Cys Thr Arg Glu Glu Thr Ser Arg Asn
        35                  40                  45

Met Leu Glu Pro Thr Ile Thr Cys Phe Asp Glu Ala Gln Lys Lys Ile
    50                  55                  60

Phe Asn Leu
65
```

(2) INFORMATION FOR SEQ ID NO:7:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

```
   Leu Ala Val Glu Asp Leu Lys Lys Arg Pro Ile Arg Glu Val Pro Ser
   1               5                   10                  15

Arg Val Gln Glu Ile Trp Gln Glu Phe Leu Ala Pro Gly Thr Pro Ser
                   20                  25                  30

Ala Ile Asn Leu Asp Ser Lys Ser Tyr Asp Lys Thr Thr Gln Asn Val
                   35                  40                  45

Lys Glu Pro Gly Arg Tyr Thr Phe Glu Asp Ala Gln Glu His Ile Tyr
                   50                  55                  60

Lys Leu
   65

(2) INFORMATION FOR SEQ ID NO:8:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

Leu Ala Cys Glu Glu Phe Lys Lys Thr Arg Ser Thr Ala Lys Leu Val
   1               5                   10                  15

Thr Lys Ala His Arg Ile Phe Glu Glu Phe Val Asp Val Asp Ala Pro
                   20                  25                  30

Arg Glu Val Asn Ile Asp Phe Gln Thr Arg Glu Ala Thr Arg Lys Asn
                   35                  40                  45

Met Gln Glu Pro Ser Leu Thr Cys Phe Asp Gln Ala Gln Gly Lys Val
                   50                  55                  60

His Ser Leu
   65

(2) INFORMATION FOR SEQ ID NO:9:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

Glu Ala Cys Glu Asp Leu Lys Tyr Gly Asp Gln Ser Lys Val Lys Glu
   1               5                   10                  15

Lys Ala Glu Glu Ile Tyr Lys Leu Phe Leu Ala Pro Gly Ala Arg Arg
                   20                  25                  30

Trp Ile Asn Ile Asp Gly Lys Thr Met Asp Ile Thr Val Lys Gly Leu
                   35                  40                  45

Arg His Pro His Arg Tyr Val Leu Asp Ala Ala Gln Thr His Ile Tyr
                   50                  55                  60

Met Leu
   65

(2) INFORMATION FOR SEQ ID NO:10:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: linear
```

(ii) MOLECULE TYPE: protein (xi) SEQUENCE DESCRIPTION: SEQ ID NO:10:

```
Leu Ala Cys Glu Asp Phe Lys Lys Val Lys Ser Gln Ser Lys Met Ala
 1               5                  10                  15

Ala Lys Ala Lys Lys Ile Phe Ala Glu Phe Ile Ala Ile Gln Ala Cys
                20                  25                  30

Lys Glu Val Asn Leu Asp Ser Tyr Thr Arg Glu His Thr Lys Glu Asn
                35                  40                  45

Leu Gln Ser Ile Thr Arg Gly Cys Phe Asp Leu Ala Gln Lys Arg Ile
            50                  55                  60

Phe Phe Gly Leu
65
```

(2) INFORMATION FOR SEQ ID NO:11:

(i) SEQUENCE CHARACTERISTICS:
      (A) LENGTH: 68 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:11:

```
Val Ala Cys Glu Asn Tyr Lys Lys Ile Lys Ser Pro Ile Lys Met Ala
 1               5                  10                  15

Glu Lys Ala Lys Gln Gln Ile Tyr Glu Glu Phe Ile Gln Thr Glu Ala
                20                  25                  30

Pro Lys Glu Val Asn Ile Asp His Phe Thr Lys Asp Ile Thr Met Lys
                35                  40                  45

Asn Leu Val Glu Pro Ser Pro His Ser Phe Asp Leu Ala Gln Lys Arg
            50                  55                  60

Ile Tyr Ala Leu
65
```

(2) INFORMATION FOR SEQ ID NO:12:

(i) SEQUENCE CHARACTERISTICS:
      (A) LENGTH: 66 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:12:

```
Leu Ala Val Gln Asp Leu Lys Lys Gln Pro Leu Gln Asp Val Ala Lys
 1               5                  10                  15

Arg Val Glu Glu Ile Trp Gln Gly Phe Leu Ala Pro Gly Ala Pro Ser
                20                  25                  30

Ala Ile Asn Leu Asp Ser His Ser Tyr Glu Ile Thr Ser Gln Asn Val
                35                  40                  45

Lys Asp Gly Gly Arg Tyr Thr Phe Glu Asp Ala Gln Glu His Ile Tyr
            50                  55                  60

Lys Leu
65
```

(2) INFORMATION FOR SEQ ID NO:13:

(i) SEQUENCE CHARACTERISTICS:

(A) LENGTH: 66 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

Leu Ala Cys Glu Asp Phe Lys Lys Thr Glu Asp Lys Lys Gln Met Gln
    1               5                   10                  15

Glu Lys Ala Lys Lys Ile Tyr Met Thr Phe Leu Ser Asn Lys Ala Ser
                20                  25                  30

Ser Gln Val Asn Val Glu Gly Gln Ser Arg Leu Thr Glu Lys Ile Leu
            35                  40                  45

Glu Glu Pro His Pro Leu Met Phe Gln Lys Leu Gln Asp Gln Ile Phe
        50                  55                  60

Asn Leu
    65

(2) INFORMATION FOR SEQ ID NO:14:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

Glu Ala Cys Glu Glu Leu Arg Phe Gly Gly Gln Ala Gln Val Pro Thr
    1               5                   10                  15

Leu Val Asp Ser Val Tyr Gln Gln Phe Leu Ala Pro Gly Ala Ala Arg
                20                  25                  30

Trp Ile Asn Ile Asp Ser Arg Thr Met Glu Trp Thr Leu Glu Gly Leu
            35                  40                  45

Arg Gln Pro His Arg Tyr Val Leu Asp Ala Ala Gln Leu His Ile Tyr
        50                  55                  60

Met Leu
    65

(2) INFORMATION FOR SEQ ID NO:15:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

ATCAGCTGTG AGGAGTACAA GAAAATCAAA TCACCTTCTA AACTAAGTCC CAAGGCCAAG      60

AAGATCTACA ATGAGTTCAT CTCTGTGCAG GCAACAAAAG AGGTGAACCT GGATTCTTGC     120

ACCAGAGAGG AGACAAGCCG GAACATGTTA GAGCCCACGA TAACCTGTTT TGATGAAGCC     180

CGGAAGAAGA TTTTCAACCT G                                                201

(2) INFORMATION FOR SEQ ID NO:16:

(i) SEQUENCE CHARACTERISTICS:
        (A) LENGTH: 198 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:16:

CAGCTTGTAA ATGTGCTCCT GAGCATCTTC GAATGTGTAT CGTCCTGGTT CCTTCACATT    60

CTGTGTGGTC TTGTCATAAC TCTTCGAATC CAAGTTAATG GCACTGGGGG CCCCCGGAGC   120

CAGAAATTCT TGCCATATTT CCTGTACTCG AGAGGGACC TCTCGGATAG GCCTTTTCTT   180

CAGGTCCTCC ACTGCCAA                                                198

(2) INFORMATION FOR SEQ ID NO:17:

(i) SEQUENCE CHARACTERISTICS:
            (A) LENGTH: 201 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

CTGGCCTGTG AGGAGTTCAA GAAGACCAGG TCGACTGCAA AGCTAGTCAC CAAGGCCCAC    60

AGGATCTTTG AGGAGTTTGT GGATGTGCAG GCTCCACGGG AGGTGAATAT CGATTTCCAG   120

ACCCGAGAGG CCACGAGGAA GAACATGCAG GAGCCGTCCC TGACTTGTTT TGATCAAGCC   180

CAGGGAAAAG TCCACAGCCT C                                            201

(2) INFORMATION FOR SEQ ID NO:18:

(i) SEQUENCE CHARACTERISTICS:
            (A) LENGTH: 198 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

GAAGCCTGTG AGGATCTGAA GTATGGGGAT CAGTCCAAGG TCAAGGAGAA GGCAGAGGAG    60

ATCTACAAGC TGTTCCTGGC ACCGGGTGCA AGGCGATGGA TCAACATAGA CGGCAAAACC   120

ATGGACATCA CCGTGAAGGG GCTGAGACAC CCCCACCGCT ATGTGTTGGA CGCGGCGCAG   180

ACCCACATTT ACATGCTC                                                198

(2) INFORMATION FOR SEQ ID NO:19:

(i) SEQUENCE CHARACTERISTICS:
            (A) LENGTH: 201 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

CTGGCTTGTG AGGATTTCAA GAAGGTCAAA TCGCAGTCCA AGATGGCAGC CAAAGCCAAG    60

AAGATCTTTG CTGAGTTCAT CGCGATCCAG GCTTGCAAGG AGGTAAACCT GGACTCGTAC   120

ACACGAGAAC ACACTAAGGA GAACCTGCAG AGCATCACCC GAGGCTGCTT TGACCTGGCA   180

CAAAAACGTA TCTTCGGGCT C                                            201

(2) INFORMATION FOR SEQ ID NO:20:

```
        (i) SEQUENCE CHARACTERISTICS:
            (A) LENGTH: 201 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

GTTGCCTGTG AGAATTACAA GAAGATCAAG TCCCCCATCA AAATGGCAGA GAAGGCAAAG        60

CAAATCTATG AAGAATTCAT CCAGACAGAG GCCCCTAAAG AGGTGAACAT TGACCACTTC       120

ACTAAAGACA TCACCATGAA GAACCTGGTG GAACCTTCCC CTCACAGCTT TGACCTGGCC       180

CAGAAAAGGA TCTACGCCCT G                                                 201

(2) INFORMATION FOR SEQ ID NO:21:

(i) SEQUENCE CHARACTERISTICS:
            (A) LENGTH: 198 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

CTGGCCGTCC AAGATCTCAA GAAGCAACCT CTACAGGATG TGGCCAAGAG GGTGGAGGAA        60

ATCTGGCAAG AGTTCCTAGC TCCCGGAGCC CCAAGTGCAA TCAACCTGGA TTCTCACAGC       120

TATGAGATAA CCAGTCAGAA TGTCAAAGAT GGAGGGAGAT ACACATTTGA AGATGCCCAG       180

GAGCACATCT ACAAGCTG                                                     198

(2) INFORMATION FOR SEQ ID NO:22:

(i) SEQUENCE CHARACTERISTICS:
            (A) LENGTH: 198 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CTAGCGTGTG AAGATTTCAA GAAAACGGAG GACAAGAAGC AGATGCAGGA AAAGGCCAAG        60

AAGATCTACA TGACCTTCCT GTCCAATAAG GCCTCTTCAC AAGTCAATGT GGAGGGGCAG       120

TCTCGGCTCA CTGAAAAGAT TCTGGAAGAA CCACACCCTC TGATGTTCCA AAAGCTCCAG       180

GACCAGATCT TCAATCTC                                                     198

(2) INFORMATION FOR SEQ ID NO:23:

(i) SEQUENCE CHARACTERISTICS:
            (A) LENGTH: 198 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GAGGCGTGTG AGGAGCTGCG CTTTGGCGGA CAGGCCCAGG TCCCCACCCT GGTGGACTCT        60

GTTTACCAGC AGTTCCTGGC CCCTGGAGCT GCCCGCTGGA TCAACATTGA CAGCAGAACA       120

ATGGAGTGGA CCCTGGAGGG GCTGCGCCAG CCACACCGCT ATGTCCTAGA TGCAGCACAA       180

CTGCACATCT ACATGCTC                                                     198
```

(2) INFORMATION FOR SEQ ID NO:24:

(i) SEQUENCE CHARACTERISTICS:
        (A) LENGTH: 555 amino acids
        (B) TYPE: amino acid
        (D) TOPOLOGY: linear (ii) MOLECULE TYPE: protein (xi) SEQUENCE DESCRIPTION: SEQ ID NO:24:

```
Met Ala Leu Pro Arg Leu Arg Val Asn Ala Ser Asn Glu Arg Leu
 1               5                  10                  15

Val His Pro Asn His Met Val Tyr Arg Lys Met Glu Met Leu Val Asn
                 20                  25                  30

Gln Met Leu Asp Ala Glu Ala Gly Val Pro Ile Lys Thr Val Lys Ser
             35                  40                  45

Phe Leu Ser Lys Val Pro Ser Val Phe Thr Gly Gln Asp Leu Ile Gly
 50                  55                  60

Trp Ile Met Lys Asn Leu Glu Met Thr Asp Leu Ser Asp Ala Leu His
 65                  70                  75                  80

Leu Ala His Leu Ile Ala Ser His Gly Tyr Leu Phe Gln Ile Asp Asp
                 85                  90                  95

His Val Leu Thr Val Lys Asn Asp Gly Thr Phe Tyr Arg Phe Gln Thr
                100                 105                 110

Pro Tyr Phe Trp Pro Ser Asn Cys Trp Asp Pro Glu Asn Thr Asp Tyr
            115                 120                 125

Ala Val Tyr Leu Cys Lys Arg Thr Met Gln Asn Lys Ala His Leu Glu
        130                 135                 140

Leu Glu Asp Phe Glu Ala Glu Asn Leu Ala Lys Leu Gln Lys Met Phe
145                 150                 155                 160

Ser Arg Lys Trp Glu Phe Val Phe Met Gln Ala Glu Ala Gln Tyr Lys
                165                 170                 175

Val Asp Lys Lys Arg Asp Arg Gln Glu Arg Gln Ile Leu Asp Ser Gln
            180                 185                 190

Glu Arg Ala Phe Trp Asp Val His Arg Pro Val Pro Gly Cys Val Asn
        195                 200                 205

Thr Thr Glu Val Asp Phe Arg Lys Leu Ser Arg Ser Gly Arg Pro Lys
210                 215                 220

Tyr Ser Gly Gly His Ala Ala Leu Ala Ala Ser Thr Ser Gly Ile
225                 230                 235                 240

Gly Cys Thr Gln Tyr Ser Gln Ser Val Ala Ala Ala His Ala Ser Leu
            245                 250                 255

Pro Ser Thr Ser Asn Gly Ser Ala Thr Ser Pro Arg Lys Asn Asp Gln
        260                 265                 270

Glu Pro Ser Thr Ser Ser Gly Glu Ser Pro Ser Thr Ser Ser Ala
            275                 280                 285

Ala Ala Gly Thr Ala Thr Thr Ser Ala Pro Ser Thr Ser Thr Pro Pro
290                 295                 300

Val Thr Thr Ile Thr Ala Thr Ile Asn Ala Gly Ser Phe Arg Asn Asn
305                 310                 315                 320

Tyr Tyr Thr Arg Pro Gly Leu Arg Arg Cys Thr Gln Val Gln Asp Thr
                325                 330                 335

Leu Lys Leu Glu Ile Val Gln Leu Asn Ser Arg Leu Ser Lys Asn Val
            340                 345                 350

Leu Arg Thr Ser Lys Val Val Glu Asn Tyr Leu Ala Tyr Tyr Glu Gln
```

5,929,207
                                    41                                                                            42
                                                                        -continued

```
                     355                 360                 365

Arg Arg Val Phe Asp Pro Leu Leu Thr Pro Pro Gly Ser Gln Ala Asp
            370                 375                 380

Pro Phe Gln Ser Gln Pro Asn Pro Trp Ile Asn Asp Thr Val Asp Phe
        385                 390                 395                 400

Trp Gln His Asp Lys Ile Thr Gly Asp Ile Gln Thr Arg Arg Leu Lys
                            405                 410                 415

Leu Trp Glu Asp Ser Phe Glu Glu Leu Leu Ala Asp Ser Leu Gly Arg
                        420                 425                 430

Glu Thr Leu Gln Lys Phe Leu Asp Lys Glu Tyr Ser Gly Glu Asn Leu
                    435                 440                 445

Arg Phe Trp Trp Glu Val Gln Lys Leu Arg Lys Cys Ser Ser Arg Met
            450                 455                 460

Val Pro Val Met Val Thr Glu Ile Tyr Asn Glu Phe Ile Asp Thr Asn
        465                 470                 475                 480

Ala Ala Thr Ser Pro Val Asn Val Asp Cys Lys Val Met Glu Val Thr
                            485                 490                 495

Glu Asp Asn Leu Lys Asn Pro Asn Arg Trp Ser Phe Asp Glu Ala Ala
                        500                 505                 510

Asp His Ile Tyr Cys Leu Met Lys Asn Asp Ser Tyr Gln Arg Phe Leu
                    515                 520                 525

Arg Ser Glu Ile Tyr Lys Asp Leu Val Leu Gln Ser Arg Lys Lys Val
                530                 535                 540

Ser Leu Asn Cys Ser Phe Ser Ile Phe Ala Ser
        545                 550                 555
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Modified-site
        (D) OTHER INFORMATION: Xaa at position 1 is I, L.
            E, or V, preferably L; Xaa at position 2 is A, S, or E,
            preferably A; Xaa at position 3 is C or V, preferably C; Xaa at
            position 5 is D, E, N, or K, preferably D; Xaa at position 6 is L, Y, or F;
            Xaa at position 7 is K or R, preferably R; and Xaa at position 8 is K, Y, R,
            or F, preferably K.

(xi) SEQUENCE DESCRIPTION: SEQ ID NO:25:

```
Xaa Xaa Xaa Glu Xaa Xaa Xaa Xaa
1               5
```

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Modified-site
        (D) OTHER INFORMATION: Xaa at position 1 is F or
            L; preferably F; Xaa at position 2 is D, E, T, or Q, preferably
            D; Xaa at position 3 is E, D, T, Q, A, L, or K; Xaa at position
            4 is A or L, preferably A; Xaa at position 5 is Q or A, preferably Q; Xaa at position 6 is L, D, E, K, T, G, or H; Xaa at position 7 is H, R, K, Q, or D; Xaa at position 8 is I or V, preferably I; Xaa at position 9 is Q, T, S, N, K, M, G, or A.

(xi) SEQUENCE DESCRIPTION: SEQ ID NO:26:

```
Xaa Xaa Xaa Xaa Xaa Xaa Xaa Xaa Xaa Xaa Lys
 1               5                   10
```

(2) INFORMATION FOR SEQ ID NO:27:

(i) SEQUENCE CHARACTERISTICS:
        (A) LENGTH: 3169 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 199..1864

(xi) SEQUENCE DESCRIPTION: SEQ ID NO:27:

```
TTTGAGACTT TTGTGGCTCA ACACCTCGTT TCTTTTGCAC CCGAACCGCA CCCACGGTAA      60

CACGGATTCT GCGAGGAATG AAGGAGTAGA AGATAACGGG ACATTCCCTT GTGTCAAAGT     120

GAGAGCCAAC GACGACGATC CTAAGAAGTA TAAACTTGGA AGAGTATTCA CAAAAGTCTT     180

GAAGACTAAA GCTTCACA ATG GCT CTA CCA AGA TTG AGG GTA AAT GCA AGC       231
                   Met Ala Leu Pro Arg Leu Arg Val Asn Ala Ser
                    1               5                   10

AAC GAG GAG CGT CTT GTA CAT CCA AAC CAC ATG GTG TAC CGT AAG ATG       279
Asn Glu Glu Arg Leu Val His Pro Asn His Met Val Tyr Arg Lys Met
             15                  20                  25

GAG ATG CTT GTC AAT CAA ATG CTT GAT GCA GAA GCT GGT GTT CCA ATC       327
Glu Met Leu Val Asn Gln Met Leu Asp Ala Glu Ala Gly Val Pro Ile
         30                  35                  40

AAG ACT GTC AAG AGT TTT CTG TCA AAA GTT CCA TCT GTA TTC ACC GGA       375
Lys Thr Val Lys Ser Phe Leu Ser Lys Val Pro Ser Val Phe Thr Gly
     45                  50                  55

CAA GAT CTG ATT GGA TGG ATC ATG AAA AAT CTT GAG ATG ACT GAT CTT       423
Gln Asp Leu Ile Gly Trp Ile Met Lys Asn Leu Glu Met Thr Asp Leu
 60                  65                  70                  75

TCG GAT GCC CTT CAT CTG GCT CAT CTG ATC GCG TCA CAC GGT TAT CTT       471
Ser Asp Ala Leu His Leu Ala His Leu Ile Ala Ser His Gly Tyr Leu
                 80                  85                  90

TTC CAA ATT GAC GAT CAT GTG TTA ACG GTT AAA AAC GAT GGA ACA TTC       519
Phe Gln Ile Asp Asp His Val Leu Thr Val Lys Asn Asp Gly Thr Phe
             95                 100                 105

TAT CGG TTT CAA ACT CCA TAC TTT TGG CCG TCA AAT TGT TGG GAT CCG       567
Tyr Arg Phe Gln Thr Pro Tyr Phe Trp Pro Ser Asn Cys Trp Asp Pro
         110                 115                 120

GAA AAT ACT GAT TAC GCG GTG TAC CTG TGC AAG CGG ACA ATG CAG AAC       615
Glu Asn Thr Asp Tyr Ala Val Tyr Leu Cys Lys Arg Thr Met Gln Asn
 125                 130                 135

AAA GCG CAT TTG GAA CTG GAG GAC TTT GAA GCG GAG AAC CTG GCA AAG       663
Lys Ala His Leu Glu Leu Glu Asp Phe Glu Ala Glu Asn Leu Ala Lys
140                 145                 150                 155

CTG CAG AAG ATG TTC TCG CGC AAG TGG GAA TTT GTG TTC ATG CAA GCC       711
Leu Gln Lys Met Phe Ser Arg Lys Trp Glu Phe Val Phe Met Gln Ala
                 160                 165                 170

GAA GCT CAA TAC AAG GTC GAC AAG AAG CGA GAT CGC CAG GAG CGC CAA       759
Glu Ala Gln Tyr Lys Val Asp Lys Lys Arg Asp Arg Gln Glu Arg Gln
             175                 180                 185
```

-continued

| | |
|---|---|
| ATT CTT GAC AGT CAG GAA CGT GCT TTC TGG GAT GTT CAT CGT CCA GTG<br>Ile Leu Asp Ser Gln Glu Arg Ala Phe Trp Asp Val His Arg Pro Val<br>190                        195                        200 | 807 |
| CCA GGA TGT GTA AAC ACT ACA GAA GTC GAC TTC CGG AAG CTT TCA CGG<br>Pro Gly Cys Val Asn Thr Thr Glu Val Asp Phe Arg Lys Leu Ser Arg<br>205                        210                        215 | 855 |
| TCT GGA AGG CCC AAG TAC AGT AGT GGA GGA CAC GCA GCA TTG GCC GCT<br>Ser Gly Arg Pro Lys Tyr Ser Ser Gly Gly His Ala Ala Leu Ala Ala<br>220                        225                        230                        235 | 903 |
| TCA ACG TCG GGT ATC GGT TGC ACT CAG TAT TCA CAA AGT GTG GCA GCA<br>Ser Thr Ser Gly Ile Gly Cys Thr Gln Tyr Ser Gln Ser Val Ala Ala<br>                        240                        245                        250 | 951 |
| GCT CAT GCG AGT CTT CCA TCA ACA TCA AAT GGG AGT GCA ACA TCT CCA<br>Ala His Ala Ser Leu Pro Ser Thr Ser Asn Gly Ser Ala Thr Ser Pro<br>               255                        260                        265 | 999 |
| AGA AAG AAC GAT CAG GAG CCA TCA ACA TCA AGT GGG GGT GAA TCT CCA<br>Arg Lys Asn Asp Gln Glu Pro Ser Thr Ser Ser Gly Gly Glu Ser Pro<br>          270                        275                        280 | 1047 |
| TCA ACA TCG TCT GCT GCT GCT GGA ACT GCC ACA ACA TCT GCA CCA TCA<br>Ser Thr Ser Ser Ala Ala Ala Gly Thr Ala Thr Thr Ser Ala Pro Ser<br>285                        290                        295 | 1095 |
| ACA TCA ACG CCT CCG GTG ACA ACT ATT ACT GCA ACG ATA AAT GCA GGA<br>Thr Ser Thr Pro Pro Val Thr Thr Ile Thr Ala Thr Ile Asn Ala Gly<br>300                        305                        310                        315 | 1143 |
| TCA TTC CGA AAT AAC TAT TAC ACA AGA CCT GGA TTA CGG CGG TGT ACA<br>Ser Phe Arg Asn Asn Tyr Tyr Thr Arg Pro Gly Leu Arg Arg Cys Thr<br>                    320                        325                        330 | 1191 |
| CAA GTA CAG GAT ACG TTA AAA CTG GAA ATT GTG CAA TTG AAT AGT CGA<br>Gln Val Gln Asp Thr Leu Lys Leu Glu Ile Val Gln Leu Asn Ser Arg<br>               335                        340                        345 | 1239 |
| TTA TCA AAA AAT GTA TTA CGT ACA TCT AAA GTT GTA GAA AAT TAT TTG<br>Leu Ser Lys Asn Val Leu Arg Thr Ser Lys Val Val Glu Asn Tyr Leu<br>350                        355                        360 | 1287 |
| GCA TAT TAC GAA CAA CGT CGA GTA TTT GAT CCA CTG TTA ACG CCT CCT<br>Ala Tyr Tyr Glu Gln Arg Arg Val Phe Asp Pro Leu Leu Thr Pro Pro<br>365                        370                        375 | 1335 |
| GGA TCT CAG GCT GAT CCT TTT CAA TCA CAG CCT AAT CCA TGG ATT AAC<br>Gly Ser Gln Ala Asp Pro Phe Gln Ser Gln Pro Asn Pro Trp Ile Asn<br>380                        385                        390                        395 | 1383 |
| GAT ACT GTT GAT TTT TGG CAA CAT GAT AAA ATT ACG GGA GAC ATC CAA<br>Asp Thr Val Asp Phe Trp Gln His Asp Lys Ile Thr Gly Asp Ile Gln<br>                    400                        405                        410 | 1431 |
| ACC CGC CGA CTC AAG CTT TGG GAG GAT AGT TTT GAA GAA TTA CTT GCT<br>Thr Arg Arg Leu Lys Leu Trp Glu Asp Ser Phe Glu Glu Leu Leu Ala<br>               415                        420                        425 | 1479 |
| GAT TCA TTA GGT CGA GAA ACT CTT CAA AAA TTC CTT GAC AAA GAA TAT<br>Asp Ser Leu Gly Arg Glu Thr Leu Gln Lys Phe Leu Asp Lys Glu Tyr<br>          430                        435                        440 | 1527 |
| TCT GGA GAA AAC TTG CGG TTT TGG TGG GAG GTA CAA AAG CTG CGA AAG<br>Ser Gly Glu Asn Leu Arg Phe Trp Trp Glu Val Gln Lys Leu Arg Lys<br>445                        450                        455 | 1575 |
| TGC AGT TCA AGA ATG GTT CCA GTT ATG GTA ACA GAG ATT TAC AAC GAG<br>Cys Ser Ser Arg Met Val Pro Val Met Val Thr Glu Ile Tyr Asn Glu<br>460                        465                        470                        475 | 1623 |
| TTT ATC GAT ACA AAT GCG GCA ACG TCG CCG GTC AAT GTG GAT TGT AAA<br>Phe Ile Asp Thr Asn Ala Ala Thr Ser Pro Val Asn Val Asp Cys Lys<br>                    480                        485                        490 | 1671 |
| GTG ATG GAA GTG ACC GAA GAC AAT TTA AAG AAT CCA AAT CGG TGG AGT<br>Val Met Glu Val Thr Glu Asp Asn Leu Lys Asn Pro Asn Arg Trp Ser<br>               495                        500                        505 | 1719 |

-continued

```
TTT GAT GAA GCA GCG GAT CAT ATC TAC TGC CTT ATG AAG AAC GAT AGT    1767
Phe Asp Glu Ala Ala Asp His Ile Tyr Cys Leu Met Lys Asn Asp Ser
        510                 515                 520

TAT CAA CGC TTT CTT CGT TCA GAA ATT TAT AAG GAT TTA GTA TTA CAA    1815
Tyr Gln Arg Phe Leu Arg Ser Glu Ile Tyr Lys Asp Leu Val Leu Gln
525                 530                 535

TCA AGA AAG AAG GTA AGT CTC AAT TGC TCG TTT TCC ATT TTT GCA TCT T  1864
Ser Arg Lys Lys Val Ser Leu Asn Cys Ser Phe Ser Ile Phe Ala Ser
540                 545                 550                 555

GATTCCTCTG AAACCCCTTT CAGTTCCGGT TTTAGCTTAG TTTGATTCCC ACCTTTTTTC  1924
CCTTCCCTTC CCCCATGAAT GTTTTCTTTT CACACTATGA GATATGTGTT TCATCTATTT  1984
TTCCGATTGA AAGCTTACTG AATGCTCGCT GAAAAACTTC AAATAACAAA CTCAGACCAA  2044
ATAACATCAA AGTTCGAGCA ATTTATTTTT TTTATACCAA AAGCATGTTC AATTGAATAT  2104
CCCATTCAGT CACTAACACT CTGATTTCAT TCAGTTAATT ATATTTTTAC AAGTAGGATC  2164
AATACACCTC AATCCCAATC AATCTAACAC ATGTTCATCC CGATCTCACT AAAATTTCAA  2224
CATTTAATAT TTCCAATCCA AAACCTAAAA CGTTAAACAT TGATCTTGT TTCAAATTCA   2284
AAATTTTCTA ACATTGATTC AGACAACGTT TACCTCACTG ATTGCTCGTA AAGCATCGCG  2344
ACGCATCGGA TCGACAATGT CGCGGAGCTC GCAGAGCAAC AAAACTCTGC ATGCGAGCGC  2404
CTCTCTCGGC TCGGCGCTTT CCGGTCACGG CTCTTCCACA TCATCAATGC TCACCGCCGG  2464
AGGAGCGGCG TCGAGCCAGA ATCTGCTGCT CGCCCCGCCA CAACATCATC TGTATGTGCC  2524
CTCACTCTCT CTCTCATACA CTCACACTCA ACACTCACTC CCAATGAAAT GCAGAATGAA  2584
TGTAGTCTTT TGACAGAAAT TGTGGAGAAT AGGGATGAGG AAAAATGAGG AAAGATATAA  2644
GTTTAAAACT TGAAAAACGT TCCAAAAATT GAAACCAATA TTCATTTCTT TCAATATCTC  2704
TGATCTTTCC AACAAGTCCG GTTCATTCCA CAGACTTTGC AAAATCTCTG TAAAATTTTC  2764
CTACTTTTTC TTGACGCAAC TATGTTCATT CATGTCATTT GACTTCTCCT CTCATTGTCC  2824
AAAATCTTGT CACTGGTTAC ATTGGTCACG TCCACAGCGT CACACATCTT GCAATAATCA  2884
CTAATCACTT TTTGTCCTGT CACTGTCCAG TCTGCTCTTT CACTGAGTTT CACTGAAATT  2944
TTCGAAAGCA TGTCACTTGA TTTTTTCGGT TTGCTGCTCA CATTGCACGG CCCTTTGAAT  3004
GCACCTGTTG ACTTTGGTTT CTGGAAAATA CTGAAAATGT GTTTTGTGTG AATTTGTAAA  3064
TCTGAAATTG CAATGATTTT GGATGATTTC ATCTTTGAGA CTGTTTGCTC TGCTATTGTC  3124
TTCTCTGAAC TACTCGAAAA TTTGAATTGA AAAAAAAAAA AAAAA                  3169
```

(2) INFORMATION FOR SEQ ID NO:28:

(i) SEQUENCE CHARACTERISTICS:
        (A) LENGTH: 29 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:28:

```
Phe Glu Met Ala Gln Thr Ser Val Phe Lys Leu Met Ser Ser Asp Ser
1               5                   10                  15

Val Pro Lys Phe Leu Arg Asp Pro Lys Tyr Ser Ala Ile
            20                  25
```

(2) INFORMATION FOR SEQ ID NO:29:

(i) SEQUENCE CHARACTERISTICS:
        (A) LENGTH: 29 amino acids (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:29:

Phe Glu Ile Val Ser Asn Glu Met Tyr Arg Leu Met Asn Asn Asp Ser
    1               5                   10                  15

Phe Gln Lys Phe Thr Gln Ser Asp Val Tyr Lys Asp Ala
                20                  25

(2) INFORMATION FOR SEQ ID NO:30:

(i) SEQUENCE CHARACTERISTICS:
        (A) LENGTH: 119 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:30:

Ser Trp Gln Asp Ser Phe Asp Thr Leu Met Ser Phe Lys Ser Gly Gln
    1               5                   10                  15

Lys Cys Phe Ala Glu Phe Leu Lys Ser Glu Tyr Ser Asp Glu Asn Ile
                20                  25                  30

Leu Phe Trp Gln Ala Cys Glu Glu Leu Lys Arg Glu Lys Asn Ser Lys
                35                  40                  45

Met Glu Glu Lys Ala Arg Ile Ile Tyr Glu Asp Phe Ile Ser Ile Leu
    50                  55                  60

Ser Pro Lys Glu Val Ser Leu Asp Ser Lys Val Arg Glu Ile Val Asn
    65                  70                  75                  80

Thr Asn Met Ser Arg Pro Thr Gln Asn Thr Phe Glu Asp Ala Gln His
                85                  90                  95

Gln Ile Tyr Gln Leu Met Ala Arg Asp Ser Tyr Pro Arg Phe Leu Thr
                100                 105                 110

Ser Ile Phe Tyr Arg Glu Thr
                115

(2) INFORMATION FOR SEQ ID NO:31:

(i) SEQUENCE CHARACTERISTICS:
        (A) LENGTH: 119 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:31:

Gln Trp Ser Gln Ser Leu Glu Lys Leu Leu Ala Asn Gln Thr Gly Gln
    1               5                   10                  15

Asn Val Phe Gly Ser Phe Leu Lys Ser Glu Phe Ser Glu Glu Asn Ile
                20                  25                  30

Glu Phe Trp Leu Ala Cys Glu Asp Tyr Lys Lys Thr Glu Ser Asp Leu
                35                  40                  45

Leu Pro Cys Lys Ala Glu Glu Ile Tyr Lys Ala Phe Val His Ser Asp
                50                  55                  60

Ala Ala Lys Gln Ile Asn Ile Asp Phe Arg Thr Arg Glu Ser Thr Ala
    65                  70                  75                  80

Lys Lys Ile Lys Ala Pro Thr Pro Thr Cys Phe Asp Glu Ala Gln Lys

```
                            85                  90                  95
        Val Ile Tyr Thr Leu Met Glu Lys Asp Ser Tyr Pro Arg Phe Leu Lys
                    100                 105                 110

Ser Asp Ile Tyr Leu Asn Leu
                    115
```

(2) INFORMATION FOR SEQ ID NO:32:

(i) SEQUENCE CHARACTERISTICS:
        (A) LENGTH: 121 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:32:

```
        Leu Trp Ser Glu Ala Phe Asp Glu Leu Leu Ala Ser Lys Tyr Gly Leu
        1               5                   10                  15

Ala Ala Phe Arg Ala Phe Leu Lys Ser Glu Phe Cys Glu Glu Asn Ile
                    20                  25                  30

Glu Phe Trp Leu Ala Cys Glu Asp Phe Lys Lys Thr Lys Ser Pro Gln
                    35                  40                  45

Lys Leu Ser Ser Lys Ala Arg Lys Ile Tyr Thr Asp Phe Ile Glu Lys
        50                  55                  60

Glu Ala Pro Lys Glu Ile Asn Ile Asp Phe Gln Thr Lys Thr Leu Ile
        65                  70                  75                  80

Ala Ala Gln Asn Ile Gln Glu Ala Thr Ser Gly Cys Phe Thr Thr Ala
                    85                  90                  95

Gln Lys Arg Val Tyr Ser Leu Met Glu Asn Asn Ser Tyr Pro Arg Phe
                    100                 105                 110

Leu Glu Ser Glu Phe Tyr Gln Asp Leu
                    115                 120
```

(2) INFORMATION FOR SEQ ID NO:33:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Modified-site
        (D) OTHER INFORMATION: /note= "Xaa at position 6 is L, Y,
            or F."

(xi) SEQUENCE DESCRIPTION: SEQ ID NO:33:

```
        Leu Ala Cys Glu Asp Xaa Lys
        1               5
```

(2) INFORMATION FOR SEQ ID NO:34:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (ix) FEATURE:
        (A) NAME/KEY: Modified-site
        (D) OTHER INFORMATION: /note= "Xaa at position 3 is E, D, T, Q, A, L, or K; Xaa at position 6 is L, D, E, K, T, G, or H;
and Xaa at position 7 is H, R, K, Q, or D."

(xi) SEQUENCE DESCRIPTION: SEQ ID NO:34:

Phe Asp Xaa Ala Gln Xaa Xaa Ile Xaa
1               5

(2) INFORMATION FOR SEQ ID NO:35:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GTGCTAGCAC TGCA                                                              14

(2) INFORMATION FOR SEQ ID NO:36:

(i) SEQUENCE CHARACTERISTICS:
        (A) LENGTH: 43 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:36:

Ser Asn Asn Ala Arg Leu Asn His Ile Leu Gln Asp Pro Ala Leu Lys
1               5                   10                  15

Leu Leu Phe Arg Glu Phe Leu Arg Phe Ser Leu Cys Glu Glu Asn Leu
            20                  25                  30

Ser Phe Tyr Ile Asp Val Ser Glu Phe Thr Thr
            35                  40

(2) INFORMATION FOR SEQ ID NO:37:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Ser Asn Leu Asn Lys Leu Asp Tyr Val Leu Thr Asp Pro Gly Met Arg
1               5                   10                  15

Tyr Leu Phe Arg Arg His Leu Glu Lys Phe Leu Cys Val Glu Asn Leu
            20                  25                  30

Asp Val Phe Ile Glu Ile Lys Arg Phe Leu Lys
            35                  40

(2) INFORMATION FOR SEQ ID NO:38:

(i) SEQUENCE CHARACTERISTICS:
        (A) LENGTH: 118 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:38:

```
Ser Trp Ala Ala Gly Asn Cys Ala Asn Val Leu Asn Asp Asp Lys Gly
  1               5                  10                  15

Lys Gln Leu Phe Arg Val Phe Leu Phe Gln Ser Leu Ala Glu Glu Asn
             20                  25                  30

Leu Ala Phe Leu Glu Ala Met Glu Lys Leu Lys Lys Met Lys Ile Ser
             35                  40                  45

Asp Glu Lys Val Ala Tyr Ala Lys Glu Ile Leu Glu Thr Tyr Gln Gly
         50                  55                  60

Ser Ile Asn Leu Ser Ser Ser Met Lys Ser Leu Arg Asn Ala Val
 65              70                  75                  80

Ala Ser Glu Thr Leu Asp Met Glu Phe Ala Pro Ala Ile Lys Glu
             85                  90                  95

Val Arg Arg Leu Leu Glu Asn Asp Gln Phe Pro Arg Phe Arg Arg Ser
             100                 105                 110

Glu Leu Tyr Leu Glu Tyr
             115
```

(2) INFORMATION FOR SEQ ID NO:39:

(i) SEQUENCE CHARACTERISTICS:
        (A) LENGTH: 123 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:39:

```
Lys Trp Ala Gln Ser Phe Glu Gly Leu Leu Gly Asn His Val Gly Arg
  1               5                  10                  15

His His Phe Arg Ile Phe Leu Arg Ser Ile His Ala Glu Glu Asn Leu
             20                  25                  30

Arg Phe Trp Glu Ala Val Val Glu Phe Arg Ser Ser Arg His Lys Ala
             35                  40                  45

Asn Ala Met Asn Asn Leu Gly Lys Val Ile Leu Ser Thr Tyr Leu Ala
             50                  55                  60

Glu Gly Thr Thr Asn Glu Val Phe Leu Pro Phe Gly Val Arg Gln Val
 65              70                  75                  80

Ile Glu Arg Arg Ile Gln Asp Asn Gln Ile Asp Ile Thr Leu Phe Asp
             85                  90                  95

Glu Ala Ile Lys His Val Glu Val Leu Arg Asn Asp Pro Tyr Val
             100                 105                 110

Arg Phe Leu Gln Ser Ser Gln Tyr Ile Asp Leu
             115                 120
```

(2) INFORMATION FOR SEQ ID NO:40:

(i) SEQUENCE CHARACTERISTICS:
        (A) LENGTH: 420 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:40:

```
Leu Ser Lys Ile Pro Ser Val Phe Ser Gly Ser Asp Ile Val Gln Trp
  1               5                  10                  15

Leu Ile Lys Asn Leu Thr Ile Glu Asp Pro Val Glu Ala Leu His Leu
             20                  25                  30
```

```
Gly Thr Leu Met Ala Ala His Gly Tyr Phe Pro Ile Ser Asp His
         35                  40                  45

Val Leu Thr Leu Lys Asp Asp Gly Thr Phe Tyr Arg Phe Gln Thr Pro
 50                  55                  60

Tyr Phe Trp Pro Ser Asn Cys Trp Glu Pro Glu Asn Thr Asp Tyr Ala
 65                  70                  75                  80

Val Tyr Leu Cys Lys Arg Thr Met Gln Asn Lys Ala Arg Leu Glu Leu
                 85                  90                  95

Ala Asp Tyr Glu Ala Glu Ser Leu Ala Arg Leu Gln Arg Ala Phe Ala
            100                 105                 110

Arg Lys Trp Glu Phe Ile Phe Met Gln Ala Glu Ala Gln Ala Lys Val
            115                 120                 125

Asp Lys Lys Arg Asp Lys Ile Glu Arg Lys Ile Leu Asp Ser Gln Glu
130                 135                 140

Arg Ala Phe Trp Asp Val His Arg Pro Val Pro Gly Cys Val Asn Thr
145                 150                 155                 160

Thr Glu Val Asp Ile Lys Lys Ser Ser Arg Met Arg Asn Pro His Lys
                165                 170                 175

Thr Arg Lys Ser Val Tyr Gly Leu Gln Asn Asp Ile Arg Ser His Ser
            180                 185                 190

Pro Thr His Thr Pro Thr Pro Glu Thr Lys Pro Pro Thr Glu Asp Glu
        195                 200                 205

Leu Gln Gln Gln Ile Lys Tyr Trp Gln Ile Gln Leu Asp Arg His Arg
210                 215                 220

Leu Lys Met Ser Lys Val Ala Asp Ser Leu Leu Ser Tyr Thr Glu Gln
225                 230                 235                 240

Tyr Leu Glu Tyr Asp Pro Phe Leu Leu Pro Pro Asp Pro Ser Asn Pro
                245                 250                 255

Trp Leu Ser Asp Asp Thr Thr Phe Trp Glu Leu Glu Ala Ser Lys Glu
            260                 265                 270

Pro Ser Gln Gln Arg Val Lys Arg Trp Gly Phe Gly Met Asp Glu Ala
        275                 280                 285

Leu Lys Asp Pro Val Gly Arg Glu Gln Phe Leu Lys Phe Leu Glu Ser
290                 295                 300

Glu Phe Ser Ser Glu Asn Leu Arg Phe Trp Leu Ala Val Glu Asp Leu
305                 310                 315                 320

Lys Lys Arg Pro Ile Lys Glu Val Pro Ser Arg Val Gln Glu Ile Trp
                325                 330                 335

Gln Glu Phe Leu Ala Pro Gly Ala Pro Ser Ala Ile Asn Leu Asp Ser
            340                 345                 350

Lys Ser Tyr Asp Lys Thr Thr Gln Asn Val Lys Glu Pro Gly Arg Tyr
        355                 360                 365

Thr Phe Glu Asp Ala Gln Glu His Ile Tyr Lys Leu Met Lys Ser Asp
370                 375                 380

Ser Tyr Pro Arg Phe Ile Arg Ser Ser Ala Tyr Gln Glu Leu Leu Gln
385                 390                 395                 400

Ala Lys Lys Lys Gly Lys Ser Leu Thr Ser Lys Arg Leu Thr Ser Leu
                405                 410                 415

Ala Gln Ser Tyr
            420
```

(2) INFORMATION FOR SEQ ID NO:41:

(i) SEQUENCE CHARACTERISTICS:
(A) LENGTH: 1913 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:41:

```
TCTTTCCAAG ATACCTAGCG TCTTCTCTGG TTCAGACATT GTTCAATGGT TGATAAAGAA      60

CTTAACTATA GAAGATCCAG TGGAGGCGCT CCATTTGGGA ACATTAATGG CTGCCCACGG     120

CTACTTCTTT CCAATCTCAG ATCATGTCCT CACACTCAAG GATGATGGCA CCTTTTACCG     180

GTTTCAAACC CCCTATTTTT GGCCATCAAA TTGTTGGGAG CCGGAAAACA CAGATTATGC     240

CGTTTACCTC TGCAAGAGAA CAATGCAAAA CAAGGCACGA CTGGAGCTCG CAGACTATGA     300

GGCTGAGAGC CTGGCCAGGC TGCAGAGAGC ATTTGCCCGG AAGTGGGAGT TCATTTTCAT     360

GCAAGCAGAA GCACAAGCAA AGTGGACAA GAAGAGAGAC AAGATTGAAA GGAAGATCCT      420

TGACAGCCAA GAGAGAGCGT TCTGGGACGT GCACAGGCCC GTGCCTGGAT GTGTAAATAC     480

AACTGAAGTG GACATTAAGA AGTCATCCAG AATGAGAAAC CCCCACAAAA CACGGAAGTC     540

TGTCTATGGT TTACAAAATG ATATTAGAAG TCACAGTCCT ACCCACACAC CCACACCAGA     600

AACTAAACCT CCAACAGAAG ATGAGTTACA ACAACAGATA AAATATTGGC AAATACAGTT     660

AGATAGACAT CGGTTAAAAA TGTCAAAAGT CGCTGACAGT CTACTAAGTT ACACGGAACA     720

GTATTTAGAA TACGACCCGT TTCTTTTGCC ACCTGACCCT TCTAACCCAT GGCTGTCCGA     780

TGACACCACT TTCTGGGAAC TTGAGGCAAG CAAAGAACCG AGCCAGCAGA GGGTAAAACG     840

ATGGGGTTTT GGCATGGACG AGGCATTGAA AGACCCAGTT GGGAGAGAAC AGTTCCTTAA     900

ATTTCTAGAG TCAGAATTCA GCTCGGAAAA TTTAAGATTC TGGCTGGCAG TGGAGGACCT     960

GAAAAAGAGG CCTATTAAAG AAGTACCCTC AAGAGTTCAG GAAATATGGC AAGAGTTTCT    1020

GGCTCCCGGA GCCCCCAGTG CTATTAACTT GGATTCCAAG AGTTATGACA AAACCACACA    1080

GAACGTGAAG GAACCTGGAC GATACACATT TGAAGATGCT CAGGAGCACA TTTACAAACT    1140

GATGAAAAGT GATTCATACC CACGTTTTAT AAGATCCAGT GCCTATCAGG AGCTTCTACA    1200

GGCAAAGAAA AAGGGGAAAT CTCTCACGTC CAAGAGGTTA ACAAGCCTTG CTCAGTCTTA    1260

CTAAACGGAT CATCTTGTAG CATGAATGCA GACTGGAGTC ACTGCACACA CTTTGTAGCT    1320

CAATGTTGTG ACCTGGAGCA GAGGACATTA GAACAAGATG TTGCATGAGC AAAGGACCTA    1380

AATTGTTATT TTTGTGTGTA CATTCCATCT CCAATGGACT CTTCCGTCTC AATGCCTCCA    1440

TTCCAAACTG TTGTCTGCTT TCTTTCTCCT TCTACTATGC TGGATCTGTG TCTCTTCCTT    1500

TTTAACAAGT TCAAGTGAAG TAAAACCTTT TCTTTTTTTC CTTCTTTCTC TCTCTCTCTC    1560

TCTCAAAGCT TCAGTTAGAC ACACAGTTCA CTGAAAATTC AGTCAGTCAA AAACTGGAAG    1620

AACTGTAAAA GAAAAAAGTA TATATCAATA AGTATACATG TGGCTTCACA TTTATTAAAC    1680

AATAAATTCC GCACAGAAAG TTTCATTTCA CCAATGTGTC ACAGTCAGAA ACAAACTCAT    1740

GTCTTCGTCT GTTGTCTGTA CATTCTCCGT TAATGTTTCT CGCATTTATT TTTATACCAT    1800

ATTTAAAGAA GAAACACCTT TTACTCCAAA TGTATTAAAG TTGATCCCTT CTCTGTAAAT    1860

TTGTGTATGT TTATATTGTT GTTTTATCTT TCATTGAAAG ATGCAGAATC TCC           1913
```

What is claimed is:

1. A substantially pure RGS polypeptide comprising the amino acid sequence shown in SEQ ID NO: 6.
2. A substantially pure RGS polypeptide comprising the amino acid sequence shown in SEQ ID NO: 7.
3. A substantially pure RGS polypeptide comprising the amino acid sequence shown in SEQ ID NO: 8.
4. A substantially pure RGS polypeptide comprising the amino acid sequence shown in SEQ ID NO: 9.
5. A substantially pure RGS polypeptide comprising the amino acid sequence shown in SEQ ID NO: 10.
6. A substantially pure RGS polypeptide comprising the amino acid sequence shown in SEQ ID NO: 11.
7. A substantially pure RGS polypeptide comprising the amino acid sequence shown in SEQ ID NO: 40.

* * * * *